United States Patent
Bettoun et al.

(10) Patent No.: US 10,954,194 B2
(45) Date of Patent: Mar. 23, 2021

(54) 18-20 MEMBER BI-POLYCYCLIC COMPOUNDS

(71) Applicants: Haro Pharmaceutical Inc., Balacynwd, PA (US); The Royal Institution for the Advancement of Learning/ McGill University, Montreal (CA); Universite De Montreal, Montreal (CA)

(72) Inventors: David Bettoun, Merion Station, PA (US); Eduardo Martinez, Bryn Mawr, PA (US); James Gleason, Montreal (CA); Sylvie Mader, Montreal (CA); Shuo Xing, Lachine (CA)

(73) Assignees: Haro Pharmaceuticals Inc., Balacynwd, PA (US); The Royal Institution for the Advancement of Learning/ McGill University, Montreal (CA); Universite De Montreal, Montreal (CA)

( * ) Notice: Subject to any disclaimer, the term of this patent is extended or adjusted under 35 U.S.C. 154(b) by 0 days.

(21) Appl. No.: 16/502,090

(22) Filed: Jul. 3, 2019

(65) Prior Publication Data

US 2019/0389805 A1    Dec. 26, 2019

Related U.S. Application Data

(60) Division of application No. 15/833,530, filed on Dec. 6, 2017, now Pat. No. 10,377,715, which is a continuation of application No. 15/316,029, filed as application No. PCT/US2015/034303 on Jun. 4, 2015, now abandoned.

(60) Provisional application No. 62/007,686, filed on Jun. 4, 2014, provisional application No. 62/007,673, filed on Jun. 4, 2014.

(51) Int. Cl.
| | | |
|---|---|---|
| *C07D 215/54* | (2006.01) | |
| *C07D 215/48* | (2006.01) | |
| *C07D 409/04* | (2006.01) | |
| *C07C 259/10* | (2006.01) | |
| *C07D 209/08* | (2006.01) | |
| *C07D 209/42* | (2006.01) | |

(52) U.S. Cl.
CPC ......... *C07D 215/54* (2013.01); *C07C 259/10* (2013.01); *C07D 209/08* (2013.01); *C07D 209/42* (2013.01); *C07D 215/48* (2013.01); *C07D 409/04* (2013.01); *C07C 2602/10* (2017.05)

(58) Field of Classification Search
CPC .................................................. C07D 215/54
See application file for complete search history.

(56) References Cited

U.S. PATENT DOCUMENTS

| 4,454,341 A | 6/1984 | Dawson et al. |
| 10,377,715 B2 * | 8/2019 | Bettoun ............... C07D 409/04 |

FOREIGN PATENT DOCUMENTS

| DE | 3443230 | 6/1985 |
| EP | 0465343 | 1/1992 |
| EP | 0963981 | 12/1999 |
| EP | 1541549 | 6/2005 |
| GB | 2197320 | 5/1988 |
| WO | 2002000196 | 1/2002 |
| WO | 2003043998 | 5/2003 |
| WO | 2011097712 | 8/2011 |
| WO | 2012030919 | 3/2012 |
| WO | 2012106343 | 8/2012 |

OTHER PUBLICATIONS

European Office Action dated Nov. 4, 2019 for Application No. 15803863.8 filed Jun. 4, 2015.
Douguet et al., Quantitative Structure-Activity Relationship Studies of RAR α, β, γ Retinoid Agonists, Quantitive Structure-Acticity Relationships. 18(2), pp. 102-123, 1999 (Abstract Only).
Marcia I. Dawson et al., 4-[3-(5,6,7,8-Tetrahydro-5,5,8,8-tetramethyl-2-naphthalenyl)phenyl)benzoic Acid and Heterocyclic-Bridged Analogues are Novel Retinoic Acid Receptor Subtype and Retinoid X Receptor @ a Agonists, Bioorganic & Medicinal Chemistry Let, vol. 10, No. 12, 2000, pp. 1311-1313.
Wetherall N. T. et al., The effects of retinoid treatment and antiestrogens on the growth of T47D human breast cancer cells, European Journal of Cancer and Clinical Oncology, vol. 22, No. 1, 1986, pp. 53-59.
Allyson L. Anding et al., 4-Hydroxybenzyl Modification of the Highly Teratogenic Retinoid, 4-[(1E)-2-(5,5,8,8-Tetramethyl-5,6,7,8-tetrahydro-2-naphthalenyl)-1-propen-1-yl]benzoic Acid (TTNBP), Yields a Compound That Induces Apoptosis in Breast Cancer Cells and Shows Reduced Teratogenicity, Chemical Research in Toxicology, vol. 24, No. 11, 2011, pp. 1853-1861.
Diaz P. et al., Synthesis and biological activities of new heterocyclic aromatic retinoids, Bioorganic & Medicinal Chemistry Letters, Pergamon, Amsterdam, NL, vol. 7, No. 17, Sep. 9, 1997, pp. 2289-2294.
Haffner Curt D. et al., Structure-Based Design of Potent Retinoid X Receptor.alpha. Agonists, Journal of Medicinal Chemistry, American Chemical Society, vol. 47 Jan. 1, 2004, pp. 2010-2029.
Ates-Alagoz Zeynep et al., Synthesis of some novel tetrahydronphthalene bezimidazole derivatives, Heterocyclic Communications, De Gruyter, DE, vol. 7, No. 6, Jan. 1, 2001, pp. 455-460.

(Continued)

*Primary Examiner* — Golam M Shameem
(74) *Attorney, Agent, or Firm* — A.C. Entis-IP Ltd.; Allan C. Entis; Kenichi N. Hartman

(57) ABSTRACT

The invention relates to a method of treating a subject who has cancer or a non-malignant tumor, the method comprising administering a therapeutically effective amount of a 18-20 member bi-polycyclic compound to the subject.

19 Claims, 16 Drawing Sheets

Specification includes a Sequence Listing.

(56) References Cited

OTHER PUBLICATIONS

Chateen Krueger et al., Identification of Retinoic Acid in a High Content Screen for Agents that Overcome the Anti-Myogenic Effect of TGF-Beta-1, PLOS ONE, vol. 5, No. 11, Nov. 30, 2010, p. e15511.

Supplementary European Search Report and European Search Opinion dated Mar. 15, 2018, for application No. 15803863.8 filed Jun. 4, 2015.

Vannini et al., Substrate binding to histone deacetylases as shown by the crystal structure of the HDAC8-substrate complex; European Molecular Biology Organization (EMBO) Reports vol. 8. No. 9 pp. 879-884, 2007.

Shibata et al., Role of Co-ativators and Co-repressors in the Mechanism of Steroid/ Thyroid Receptor Action; Recent Progress in Hormone Research, vol. 52: pp. 141-164, 1997.

Gronemeyer et al., Molecular Mechanisms of Retinoid Action; Cell and Molecular Biology Letters, vol. 6: pp. 3-52, 2001.

Oehme et al., Histone Deacetylase 8 in Neuroblastoma Tumorigenesis; Clinical Cancer Research 15(1):pp. 91-99, 2009.

Pori et al., Azetidinone-retinoid hybrids: Synthesis and Differentiative Effects; European Journal of Medicinal Chemistry, 70: pp. 857-863, 2013.

Evans , Skeletal muscle loss: cachexia, sarcopenia, and inactivity; American Journal Clinical Nutrition, 91(suppl): pp. 1123S-1127S, 2010.

Abmayr et al., Myoblast fusion: lessons from flies and mice; Development 139: pp. 641-656, 2012.

Macpherson et al., Myogenin regulates Denervation-Depemdent Musc;e Atrophy in Mouse Soleus Muscle; J. Cell Biochem. 112(8):pp. 2149-2159, 2011.

Moresi et al., Myogenin and Class II HDACs Control Neurogenic Muscle Atrophy by Inducing E3 Ubiquiten Ligases; Cell 143:pp. 35-45, 2010.

Nebbioso et al., Selective class II HDAC inhibitors impair myogenesis by modulating the stability and activity of HDAC-MEF2 comlexes; European Molecular Biology Organization (EMBO) Reports 10(7):pp. 776-782, 2009.

Glenisson et al., Histone deacetylase 4 is required for TGFβ 1-induced myofibroblastic differentiation; Biochimica et Biophysica Acta 1773:1572-1582, 2007.

International (PCT) Search Report and Written Opinion dated Sep. 10, 2015 for International Application No. PCT/US2015/034303 filed Jun. 4, 2015.

* cited by examiner

Compound 13

Compound 5

Compound 17

Compound 8

Compound B

SAHA

Compound 18

Compound 19

, and

Compound 20

Compound 21

SEQUENCE LISTING

<160> NUMBER OF SEQ ID NOS: 6

<210> SEQ ID NO 1
<211> LENGTH: 20
<212> TYPE: DNA
<213> ORGANISM: Artificial sequence
<220> FEATURE:
<223> OTHER INFORMATION: Reverse Primer for MYOGENIN

<400> SEQUENCE: 1
ctgggaaggc aacagacata        20

<210> SEQ ID NO 2
<211> LENGTH: 22
<212> TYPE: DNA
<213> ORGANISM: Artificial sequence
<220> FEATURE:
<223> OTHER INFORMATION: Reverse Primer for RPLP0

<400> SEQUENCE: 2
cagaccggag ttttaagaga ag        22

<210> SEQ ID NO 3
<211> LENGTH: 20
<212> TYPE: DNA
<213> ORGANISM: Artificial sequence
<220> FEATURE:
<223> OTHER INFORMATION: Forward Primer for ATROGIN

<400> SEQUENCE: 3
cttctcagag aggcagattc        20

<210> SEQ ID NO 4
<211> LENGTH: 18
<212> TYPE: DNA
<213> ORGANISM: Artificial sequence
<220> FEATURE:
<223> OTHER INFORMATION: Forward Primer for MYOGENIN

<400> SEQUENCE: 4
cccaacccag gagatcat        18

<210> SEQ ID NO 5
<211> LENGTH: 21
<212> TYPE: DNA
<213> ORGANISM: Artificial sequence
<220> FEATURE:
<223> OTHER INFORMATION: Forward Primer for RPLP0

<400> SEQUENCE: 5
cggaggaatc agatgaggat a        21

<210> SEQ ID NO 6

```
<211> LENGTH: 22
<212> TYPE: DNA
<213> ORGANISM: Artificial sequence
<220> FEATURE:
<223> OTHER INFORMATION: Reverse Primer for ATROGIN

<400> SEQUENCE: 6
tcttcttggg taacatcgta ca                                    22
```

18-20 MEMBER BI-POLYCYCLIC COMPOUNDS

CROSS REFERENCE TO RELATED APPLICATIONS

This application is a Divisional Application of allowed U.S. application Ser. No. 15/833,530, filed on Dec. 6, 2017, which is a continuation application of U.S. application Ser. No. 15/316,029, filed Dec. 2, 2016, now abandoned, which is a U.S. national phase application of International Application No. PCT/US2015/034303, filed Jun. 4, 2015, which claims the benefit of the filing date of U.S. Provisional Application No. 62/007,673, filed Jun. 4, 2014, and U.S. Provisional Application No. 62/007,686, filed Jun. 4, 2014, the discloures of which are hereby incorporated by reference in their entireties.

FIELD OF THE INVENTION

The invention relates to 18-20 member bi-polycyclic compounds and methods of making and using these compounds to promote muscle formation, inhibit muscle degeneration, and treat hyperproliferative disorders (e.g., cancer).

BACKGROUND OF THE INVENTION

The disappearance of muscle mass associated with several pathological conditions is not effectively addressed by palliative or pharmacological therapies. Therefore there is a need to develop therapeutics that delay or prevent the mechanisms of muscle atrophy and can therefore inhibit or help to prevent muscle degeneration and support muscle function in patients.

The following references may be of interest: Vannini et al., *EMBO Rep.* 8(9):879-84, 2007; Shibata et al., *Recent Prog. Horm. Res.* 52:141-64, 1997; Gronemeyer and Miturski, *Cell Mol. Biol. Lett.* 6:3-52, 2001; Oehme et al., *Clin. Cancer Res.* 15(1):91-9, 2009; Pori, *Eur. J. Med. Chem.* 70:857-63, 2013; Evans et al., *Am. J. Clin. Nutr.* 91(suppl): 1123S-7S, 2010; Abmayr and Pavlath, *Development* 139: 641-656, 2012; Macpherson et al., *J. Cell. Biochem.* 112(8): 2149-59, 2011; Moresi et al. *Cell* 143:35-45, 2010; Nebbioso et al., *EMBO Rep.* 10(7):776-82, 2009; Glenisson et al., *Biochim. Biophys. Acta.* 1773:1572-82, 2007 and WO/2011/097712.

SUMMARY OF THE INVENTION

In a first aspect, the invention relates to a compound of Formula I: A-W—Z (I) or a pharmaceutically acceptable salt thereof, wherein A is

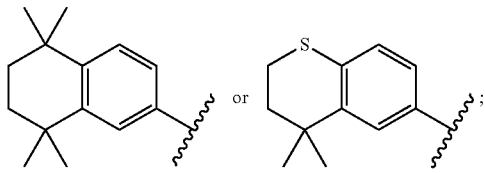 [SMILES: *c1ccc2c(c1)C(C)(C)CCC2(C)C ; *c1ccc2c(c1)C(C)(C)CCS2]

W is a heterocyclylene, arylene, heteroarylene, alkenylenearylene, arylenealkenylene alkenyleneheteroarylene, or heteroarylenealkenylene; and Z is a hydrogen bond donor, with the proviso that the compound is not

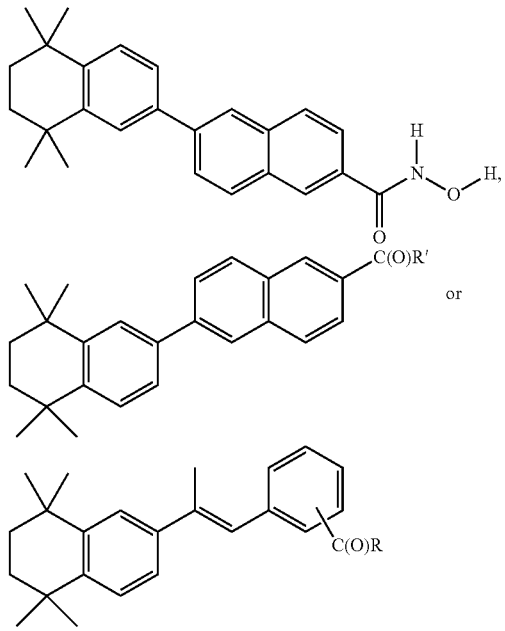

where R is —OH, —OCH$_3$ and —NHOH; and R' is —OH or —OCH$_3$.

In another aspect, the invention features methods of treating a subject who has cancer or a non-malignant tumor by administering to the subject a therapeutically effective amount of a compound described above or a pharmaceutically acceptable composition containing such a compound or a mixture thereof.

The invention also relates, in part, to methods of inhibiting loss of muscle mass or muscle function in a subject, the method comprising administering to a subject in need thereof a therapeutically effective amount of a compound of Formula I:

$$A\text{-}W\text{—}Z \qquad (I)$$

or a pharmaceutically acceptable salt thereof, wherein A is

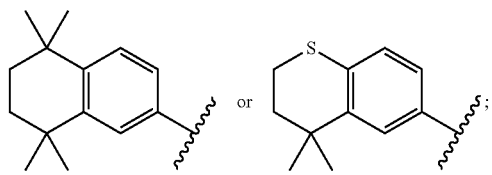 [SMILES: *c1ccc2c(c1)C(C)(C)CCC2(C)C ; *c1ccc2c(c1)C(C)(C)CCS2]

W is a heterocyclylene, arylene, heteroarylene, alkenylenearylene, arylenealkenylene or alkenyleneheteroarylene, heteroarylenealkenylene; and Z is a hydrogen bond donor.

In another aspect, the invention features methods for treating myofibers ex vivo. These methods can include the steps of providing an ex vivo preparation of myofibers, optionally comprising a natural or synthetic biological matrix; and contacting the preparation with an amount of a compound of Formula I: A-W—Z (I) or a pharmaceutically acceptable salt thereof, that is sufficient to promote muscle mass or muscle function. Within Formula I, A is

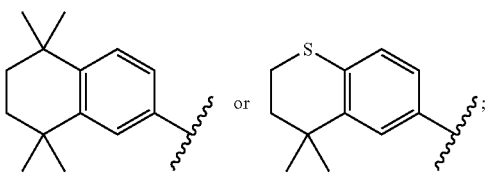 [SMILES: *c1ccc2c(c1)C(C)(C)CCC2(C)C ; *c1ccc2c(c1)C(C)(C)CCS2]

W is a heterocyclylene, arylene, heteroarylene, alkenylenearylene, arylenealkenylene alkenyleneheteroarylene, or heteroarylenealkenylene; and Z is a hydrogen bond donor.

In another aspect, the invention features methods of making a compound as described herein, for example, as illustrated in the synthetic schemes shown below.

In other aspects, the invention features the use of one or more of the compounds described herein in the preparation of a medicament or in the preparation of a medicament for the treatment of cancer to for inhibiting the loss of muscle mass or muscle function.

Where elements are listed, it is to be understood that any one or more of the listed elements can be excluded from the compound, composition, or method. For example, the inventors have specified that W can be a heterocyclylene, arylene, heteroarylene, alkenylenearylene, arylenealkenylene alkenyleneheteroarylene, or heteroarylenealkenylene. Therefore, W can be any of these elements except heterocyclylene, for example.

DETAILED DESCRIPTION

Figure 1:
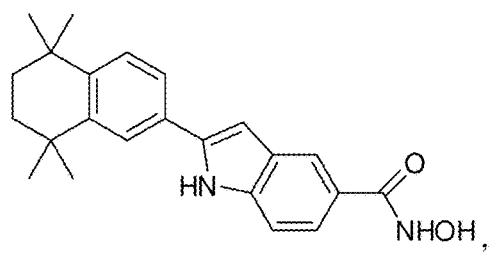
FIG. 1 exemplifies various compounds of embodiments of the invention, Compound 13, Compound 5, Compound 17, Compound 8, Compound B, SAHA, Compound 18, Compound 19, Compound 20 and Compound 21.
Figure 1:
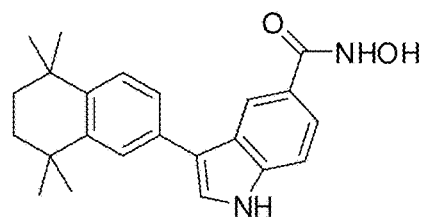
Figure 1:
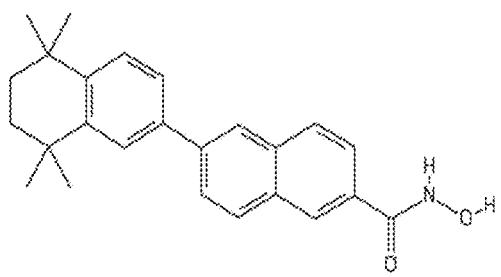
Figure 1:
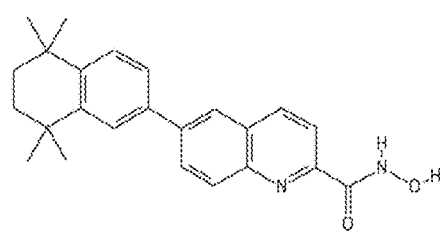
Figure 1:
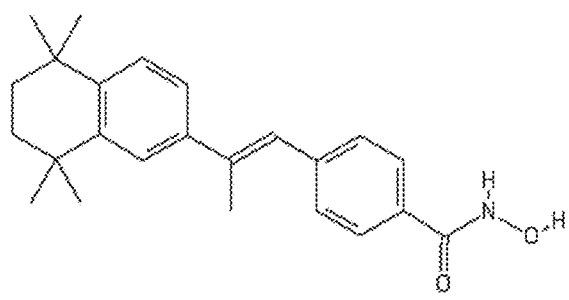
Figure 1:
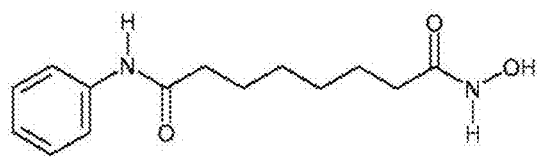
Figure 1:
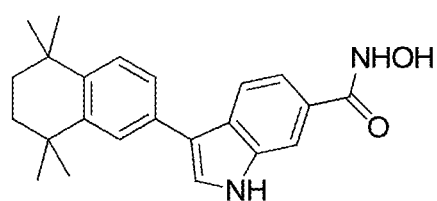
Figure 1:
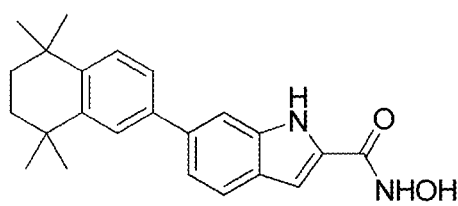
Figure 1:
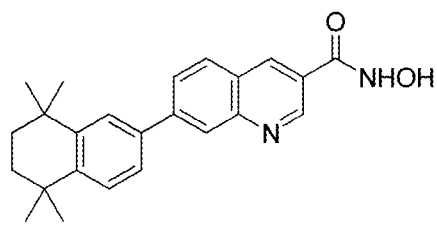
Figure 1:
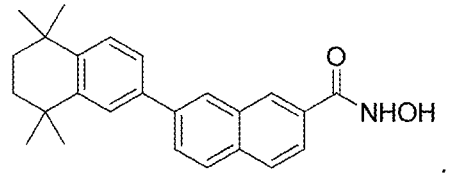
Figure 2:
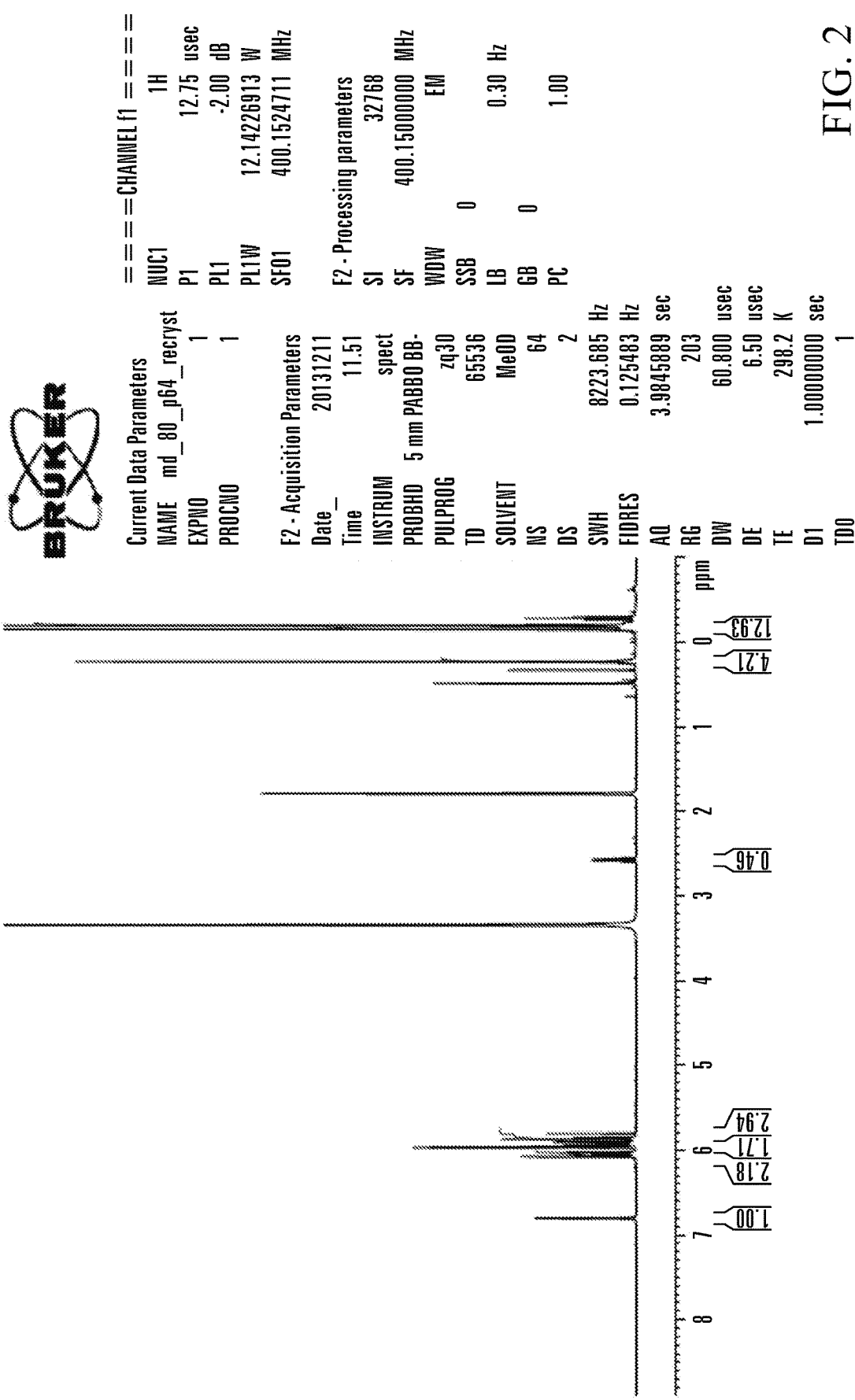
FIG. 2 shows a proton NMR spectra for compound 5.
Figure 3:
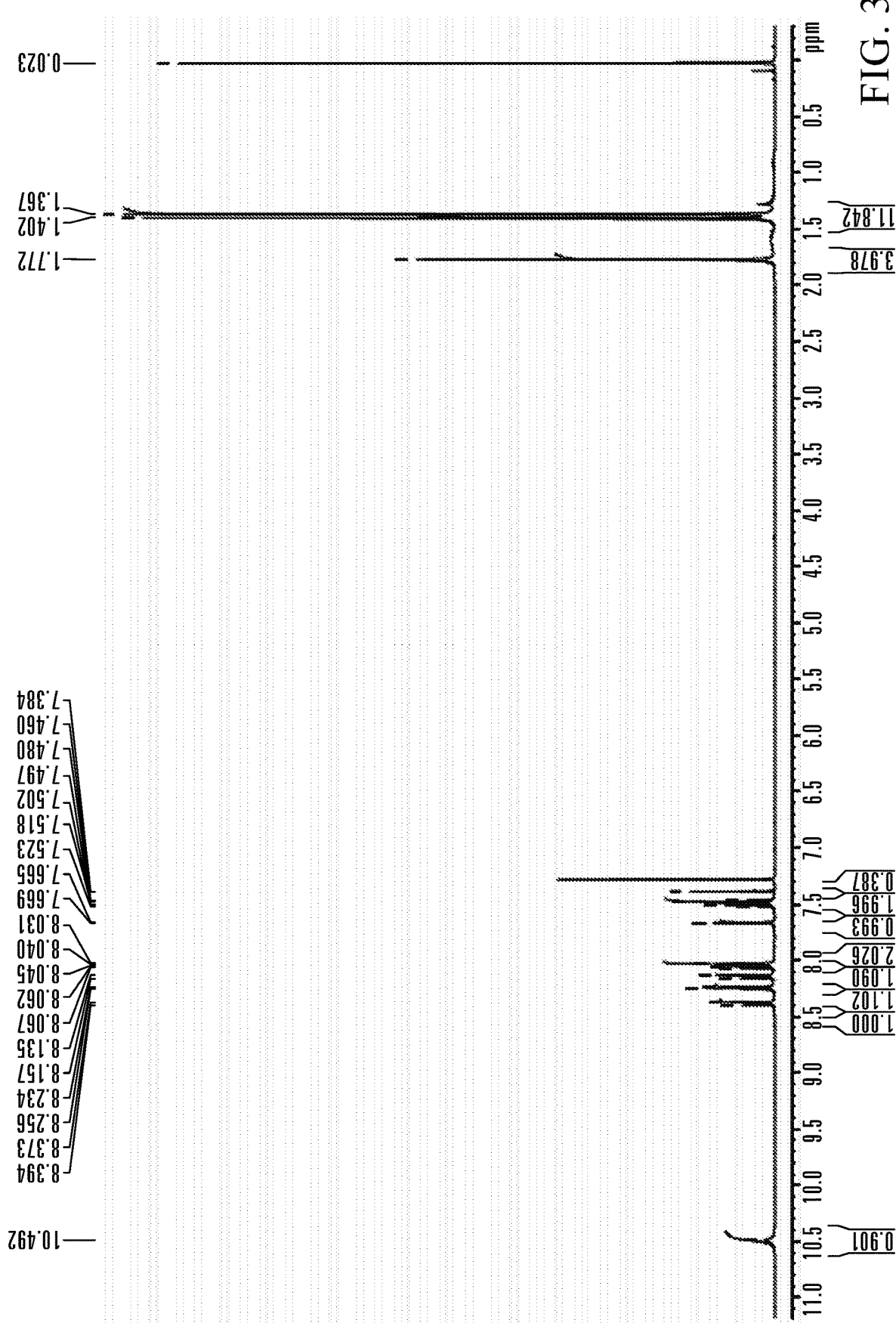
FIG. 3 shows a proton NMR spectra for compound 8.
Figure 4:
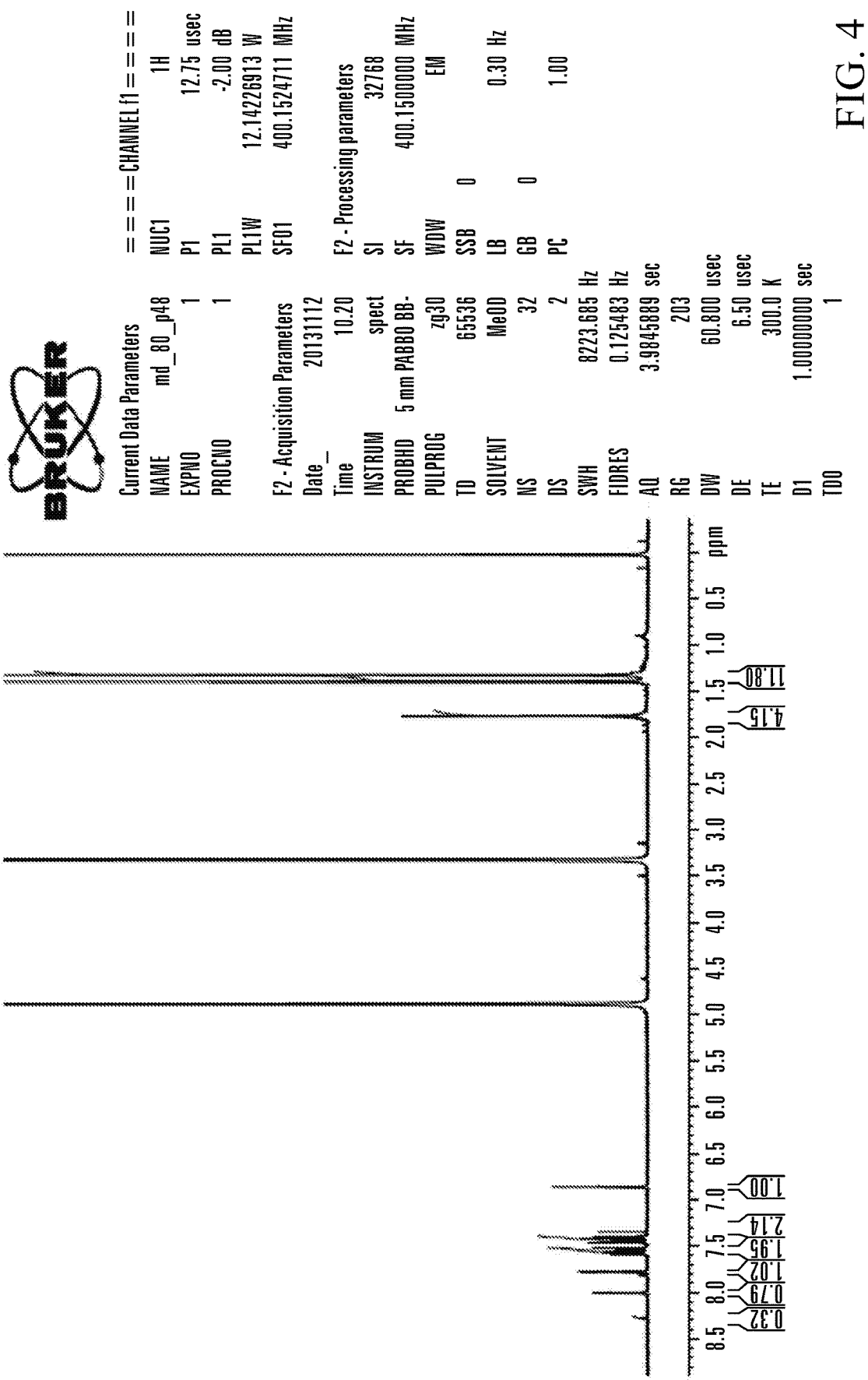
FIG. 4 shows a proton NMR spectra for compound 13.

Compounds: The invention relates to compounds of Formula I:

or a pharmaceutically acceptable salt thereof, wherein A is

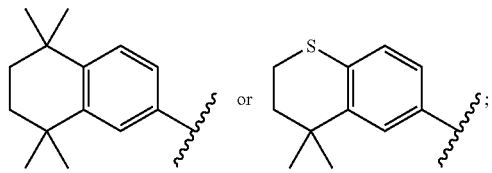 [SMILES: *c1ccc2c(c1)C(C)(C)CCC2(C)C ; *c1ccc2c(c1)C(C)(C)CCS2]

W is a heterocyclylene, arylene, heteroarylene, alkenylenearylene, arylenealkenylene alkenyleneheteroarylene, or heteroarylenealkenylene; and Z is a hydrogen bond donor, with the proviso that the compound is not a compound conforming to

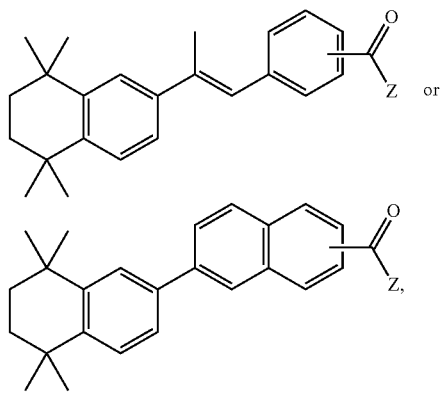

wherein Z is a hydrogen bond donor (e.g., wherein Z is —OH, —O($C_{1-6}$ alkyl), —$NH_2$, and —NHOH). For example, the invention relates to compounds of Formula I with the proviso that the compound is not:

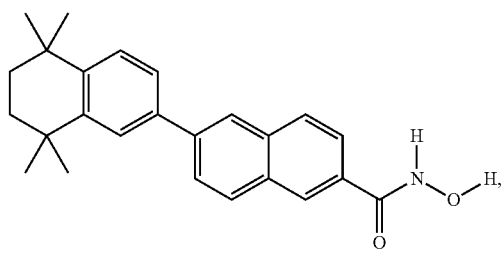

-continued

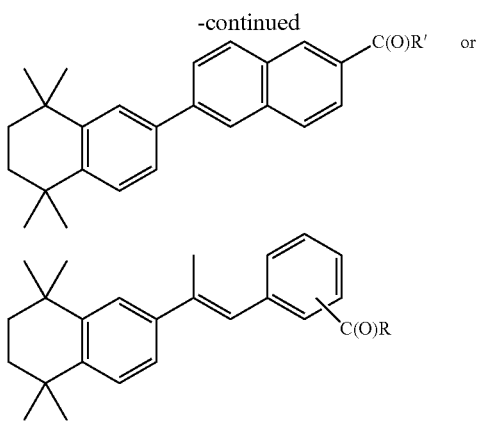

where R is —OH, —OCH$_3$ and —NHOH; and R' is —OH or —OCH$_3$.

In some embodiments, W is an indolinylene linked to A at any one of positions 2, 3, 4, 5, 6 or 7 of the indolinylene; a quinolinene linked to A at any one of positions 2, 3, 4, 5, 6, 7, or 8; or an isoquinolinene linked to A at any one of positions 1, 3, 4, 5, 6, 7, or 8. In other embodiments, W is -propylene-phenylene-.

In regard to the indolinylene, quinolinene and isoquinolinene moieties, the following numbering schemes apply:

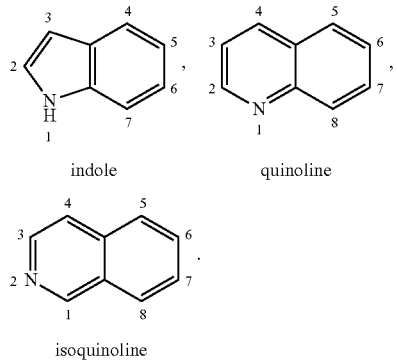

indole    quinoline isoquinoline

The compounds of the invention are not limited to the indolinylene, quinolinene and isoquinolinene moieties for W. The nitrogen atom in these ring systems may have an oxygen or sulfur atom instead of nitrogen.

In some embodiments, W is

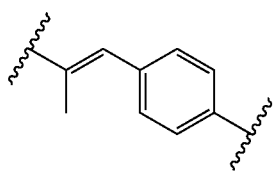 [SMILES: */C(C)=C/c1ccc(*)cc1]

In some embodiments, Z is —C(O)NR$^1$R$^2$ or —C(O)OR$^3$, where R$^1$ and R$^2$ are each independently hydrogen (H), hydroxyl (OH), C$_{1-6}$ alkyl, hydroxyC$_{1-6}$ alkyl, aminoC$_{1-6}$ alkyl, or aminoaryl; and R$^3$ is H or C$_{1-6}$ alkyl.

In some embodiments, Z is linked to the indolinylene, quinolinene, or isoquinolinene at any one of the positions of the indolinylene, quinolinene, or isoquinolinene that is not linked to A.

In some embodiments, W is an indolinylene linked to A at any one of positions 2, 3, 4, 5, 6 or 7 of the indolinylene; Z is —C(O)NR$^1$R$^2$ or —C(O)OR$^3$, where R$^1$ and R$^2$ are each independently hydrogen, hydroxyl, C$_{1-6}$ alkyl, hydroxyC$_{1-6}$ alkyl, aminoC$_{1-6}$ alkyl, or aminoaryl; and R$^3$ is H or C$_{1-6}$ alkyl, and where Z is linked to the indolinylene at any one of positions 2, 3, 4, 5, 6 or 7 of the indolinylene not linked to A.

In other embodiments, W is a quinolinene linked to A at any one of positions 2, 3, 4, 5, 6, 7 or 8 of the quinolinene; Z is —C(O)NR$^1$R$^2$ or —C(O)OR$^3$, where R$^1$ and R$^2$ are each independently hydrogen, hydroxyl, C$_{1-6}$ alkyl, hydroxyC$_{1-6}$ alkyl, aminoC$_{1-6}$ alkyl, or aminoaryl; and R$^3$ is H or C$_{1-6}$ alkyl, and where Z is linked to the quinolinene at any one of positions 2, 3, 4, 5, 6, 7 or 8 of the quinolinene.

In certain other embodiments, W is a isoquinolinene linked to A at one of positions 1, 3, 4, 5, 6, 7 or 8 of the isoquinolinene moiety; Z is —C(O)NR$^1$R$^2$ or —C(O)OR$^3$, where R$^1$ and R$^2$ are each independently hydrogen, hydroxyl, C$_{1-6}$ alkyl, hydroxyC$_{1-6}$ alkyl, aminoC$_{1-6}$ alkyl, or aminoaryl; and R$^3$ is H or C$_{1-6}$ alkyl, and where Z is linked to the quinoline ring at any one of positions 2, 3, 4, 5, 6, 7 or 8 of the isoquinolinene.

In one embodiment, Z is —C(O)NR$^1$R$^2$; R$^1$ is H; and R$^2$ is OH.

In another embodiment, Z is —C(O)NR$^1$R$^2$; R$^1$ is H; and R$^2$ is aminoaryl.

In yet another embodiment, Z is —C(O)OR$^3$; and R$^3$ is H.

In another embodiment, Z is —C(O)OR$^3$; and R$^3$ is C$_{1-6}$ alkyl.

The compound can be:

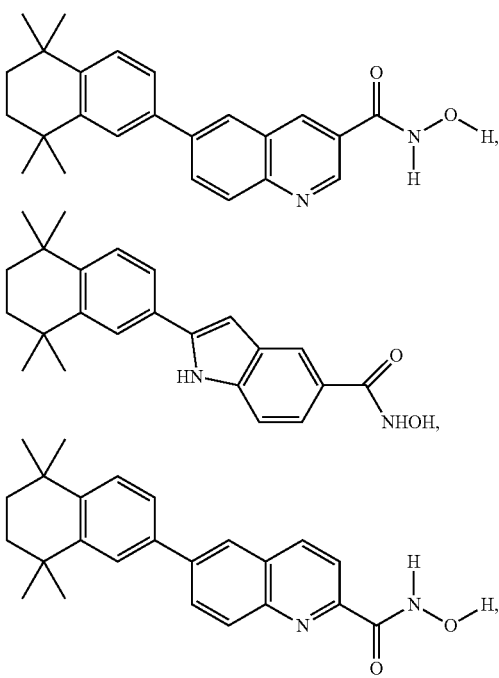

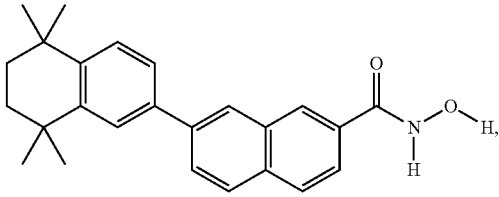

-continued

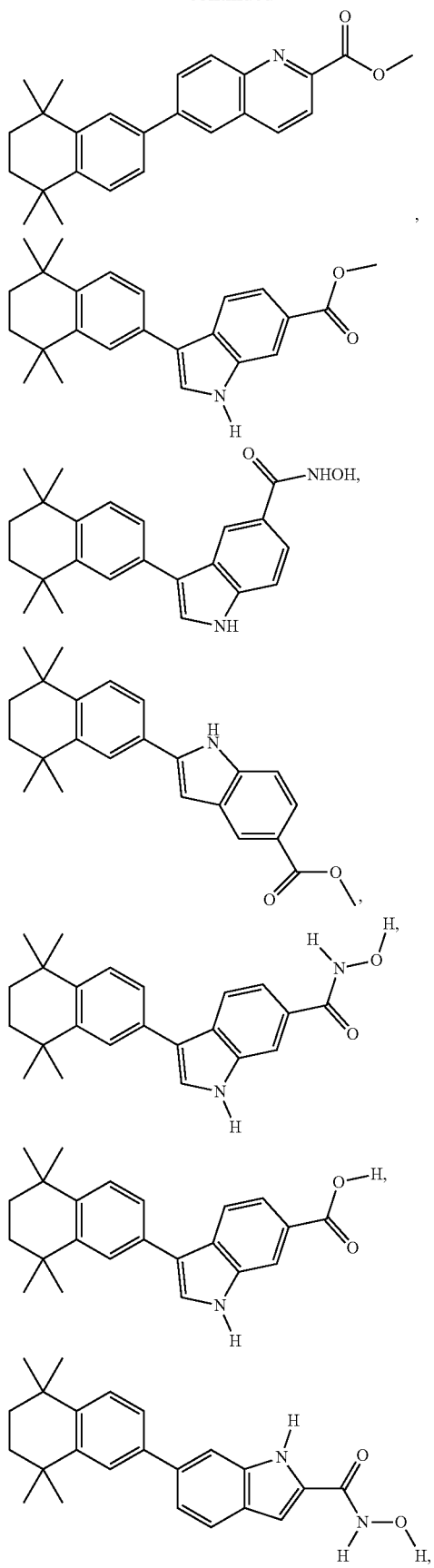

-continued

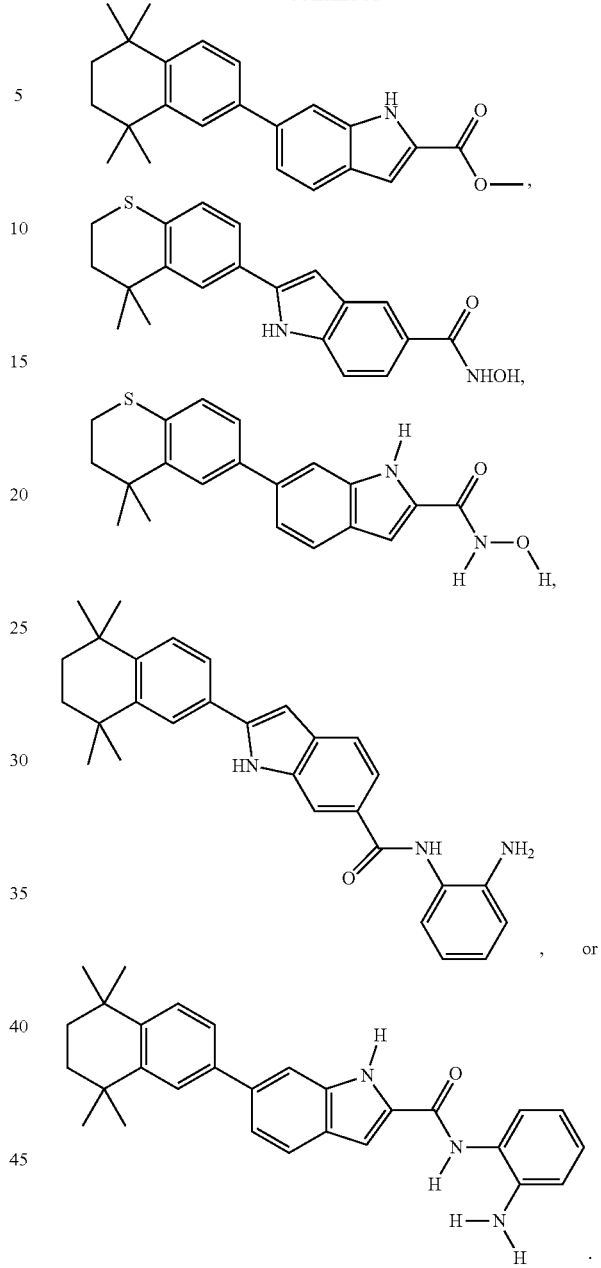

It is to be understood that certain features of the invention, which are, for clarity, described in the context of separate embodiments, can be combined in a single embodiment. Conversely, various features of the invention which are, for brevity, described in the context of a single embodiment, can also be provided separately or in any suitable subcombination.

The compounds described herein can be asymmetric (e.g., having one or more stereocenters). All stereoisomers, such as enantiomers and diastereomers, are intended unless otherwise indicated. Accordingly, the compositions of the invention (e.g., pharmaceutical compositions) can include a compound or compounds in the R-form, the S-form, or a racemic or non-racemic mixture thereof. Compounds that contain asymmetrically substituted carbon atoms can be isolated in optically active or racemic forms. Methods for preparing optically active forms from optically inactive starting materials are known in the art and include resolution of racemic mixtures and stereoselective synthesis. Stable, geometric isomers are also contemplated in the present invention. Cis and trans geometric isomers of the compounds are described and may be isolated as a mixture of isomers or as separate isomers.

Resolution of racemic mixtures can be carried out by any of the numerous methods known in the art. For example, compounds can be resolved by fractional recrystallization using a chiral resolving acid which is an optically active, salt forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as 3-camphorsulfonic acid. Other resolving agents suitable for fractional crystallization methods include stereoisomerically pure forms of ct-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like. Racemic mixtures can also be resolved by elution on a column packed with an optically active resolving agent (e.g., dinitrobenzoylphenylglycine). Suitable elution solvent compositions can be determined by one of ordinary skill in the art.

Compounds of the invention also include tautomeric forms, which result from the swapping of a single bond with an adjacent double bond together with the concomitant migration of a proton. Tautomeric forms include prototropic tantomers which are isomeric protonation states having the same empirical formula and total charge. Examples of prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by an appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

As used herein, the term "alkyl" refers to a saturated hydrocarbon group which is straight-chained or branched. Examples of alkyl groups include methyl (Me), ethyl (Et), propyl (e.g., n-propyl and isopropyl), butyl (e.g., n-butyl, isobutyl, sec-butyl, t-butyl), pentyl (e.g., n-pentyl, isopentyl, sec-pentyl, neopentyl), and the like. An alkyl group can contain from 1 to about 20 (e.g., from 2 to about 20, from 1 to about 10, from 1 to about 8, from 1 to about 6, from 1 to about 4, or from 1 to about 3) carbon atoms. By "about," we mean ±10% (e.g., about 20 grams is 18-22 grams) or, where the referenced number of units is less than 10 or not readily useful in divided tenths, we mean ±1 (e.g., about 6 carbon atoms is 5-7 carbon atoms; about 20 carbon atoms is 19-21 carbon atoms).

The term "alkoxy," when used alone or in combination with other groups, refers to a terminal oxy containing alkyl group, as defined above such as methoxy, ethoxy, propoxy, isopropoxy and the like.

The terms "alkenyl" and "alkynyl," when used alone or in combination with other groups, refer to mono- or polyunsaturated aliphatic hydrocarbon radicals containing from two to 15 carbon atoms and at least one double or triple bond, respectively. "Alkenyl" and "alkynyl" refer to both branched and unbranched alkenyl and alkynyl groups, respectively. The alkenyl and alkynyl groups include straight chained alkenyl or alkynyl groups containing from two to eight carbon atoms and branched alkenyl or alkynyl groups containing from five to ten carbon atoms. The alkenyl and alkynyl groups also include alkenyl and alkynyl groups containing from two to six carbon atoms and branched alkenyl and alkynyl groups containing from 5 to eight carbon atoms. Examples of alkenyl groups include ethenyl, 2-propenyl, 1-propenyl, 2-methyl-1-propenyl, 1-butenyl, 2-butenyl, 1-pentenyl, 2-pentenyl, 3-pentenyl, allyl, 1,3-butadienyl, 1, 3-dipentenyl, 1,4 dipentenyl, 1-hexenyl, 1, 3-hexenyl, 1,4-hexenyl, 1, 3, 5-trihexenyl, 2,4-dihexenyl, and the like.

Examples of alkynyl include ethynyl, 1-propynyl, 2-propynyl, 1 butynyl, 2-butynyl, 2-methyl-1-butynyl, 1-pentynyl, 2-pentynyl, 3-pentynyl, 3 -methyl-1-pentynyl, 2-methyl-1-pentynyl, 1-hexynyl, 2-hexynyl, 3-hexynyl, and the like. The alkenyl and alkynyl groups contain at least one double bond or one triple bond, respectively. In another embodiment, they each may contain up to 4 carbon-carbon multiple bonds, for example, 1, 2, 3, or 4, double bonds or triple bonds, respectively. The double bonds in the alkenyl groups may be conjugated, as in 1,3-butadienyl, or non-conjugated, as in 1,4-di pentenyl.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms. The term "aryl" includes aromatic rings fused to non-aromatic rings, as long as one of the fused rings is an aromatic hydrocarbon.

The term "heteroaryl" refers to an aryl group in which at least one of the ring atoms is a heteroatom (i.e., oxygen, nitrogen, or sulfur). Heteroaryl groups include monocyclic and polycyclic (e.g., having 2, 3 or 4 fused rings) systems. Examples of heteroaryl groups include without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzodiazine, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, quinolinyl, isoquinolinyl purinyl, indolyl, and the like.

The term "heterocyclic" when used alone or in combination with other groups refers to a 5- to 8-membered (e.g., 5- or 6-membered) monocyclic or 8- to 11-membered bicyclic heterocyclic radical that may be either saturated or unsaturated, aromatic or non-aromatic, and which may be optionally benzo- or pyrido-fused if monocyclic, containing at least one ring heteroatom. Each heterocycle consists of carbon atoms and from 1 to 4 ring heteroatoms selected from nitrogen, oxygen and sulfur.

As used herein, "nitrogen" and "sulfur" include any oxidized form of nitrogen and sulfur and the quaternized form of any basic nitrogen.

"Alkylene" refers to a linear or branched saturated divalent hydrocarbon radical, which may optionally be substituted as described herein. In certain embodiments, the alkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Linear $C_{1-6}$ and branched $C_{3-6}$ alkylene groups are also referred as "lower alkylene." Examples of alkylene groups include, but are not limited to, methylene, ethylene, propylene (including all isomeric forms), n-propylene, isopropylene, butylene (including all isomeric forms), n-butylene, isobutylene, t-butylene, pentylene (including all isomeric forms), and hexylene (including all isomeric forms). For example, $C_{1-6}$ alkylene refers to a linear saturated divalent hydrocarbon radical of 1 to 6 carbon atoms or a branched saturated divalent hydrocarbon radical of 3 to 6 carbon atoms.

The term "alkenylene" refers to a linear or branched divalent hydrocarbon radical that contains one or more carbon-carbon double bonds. The alkenylene may be optionally substituted as described herein. The term "alkenylene" also embraces radicals having "cis" and "trans" configurations, or alternatively, "E" and "Z" configurations. As used herein, the term "alkenylene" encompasses both linear and branched alkenylene, unless otherwise specified. For example, $C_{2-6}$ alkenylene refers to a linear unsaturated divalent hydrocarbon radical of 2 to 6 carbon atoms or a branched unsaturated divalent hydrocarbon radical of 3 to 6 carbon atoms. In certain embodiments, the alkenylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenylene groups include, but are not limited to, ethenylene, allylene, propenylene, butenylene, and 4-methylbutenylene.

The term "cycloalkylene" refers to a cyclic saturated bridged and/or non-bridged divalent hydrocarbon radical, which may be optionally substituted as described herein. In certain embodiments, the cycloalkylene has from 3 to 20 ($C_{3-20}$), from 3 to 15 ($C_{3-15}$), from 3 to 10 ($C_{3-10}$), or from 3 to 7 ($C3-_7$) carbon atoms. Examples of cycloalkylene groups include, but are not limited to, cyclopropylene (e.g., 1,1-cyclopropylene and 1,2-cyclopropylene), cyclobutylene (e.g., 1,1-cyclobutylene, 1,2-cyclobutylene, or 1,3 -cyclobutylene), cyclopentylene (e.g., 1,1-cyclopentylene, 1,2-cyclopentylene, or 1,3 -cyclopentylene), cyclohexylene (e.g., 1,1-cyclohexylene, 1,2-cyclohexylene, 1,3 -cyclohexylene, or 1,4-cyclohexylene), cycloheptylene (e.g., 1,1-cycloheptylene, 1,2-cycloheptylene, 1,3 -cycloheptylene, or 1,4-cycloheptylene), decalinylene, and adamantylene.

The term "heterocyclylene" refers to a divalent non-aromatic ring system and/or a multicyclic ring system that contains at least one non-aromatic ring, wherein one or more of the non-aromatic ring atoms are heteroatoms independently selected from O, S, or N, and the remaining ring atoms are carbon atoms. In certain embodiments, the heterocyclylene group has from 3 to 20 (e.g., 3-15, 3-10, 3-8, 4-7, or 5-6) ring atoms. In certain embodiments, the heterocyclylene is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclylene may be attached to the main structure at any heteroatom or carbon atom which results in the creation of a stable compound. Examples of such heterocyclene groups include, but are not limited to, azepinylene, benzodioxanylene, benzodioxolylene, benzofuranonylene, benzopyranonylene, benzopyranylene, benzotetrahydrofuranylene, benzotetrahydrothienylene, benzothiopyranylene, benzoxazinylene, β-carbolinylene, chromanylene, chromonylene, cinnolinylene, coumarinylene, decahydroisoquinolinylene, dihydrobenzisothiazinylene, dihydrobenzisoxazinylene, dihydrofurylene, dihydroisoindolylene, dihydropyranylene, dihydropyrazolylene, dihydropyrazinylene, dihydropyridinylene, dihydropyrimidinylene, dihydropyrrolylene, dioxolanylene, 1,4-dithianylene, furanonylene, imidazolidinylene, imidazolinylene, indolinylene, isobenzotetrahydrofuranylene, isobenzotetrahydrothienylene, isochromanylene, isocoumarinylene, isoindolinylene, isothiazolidinylene, isoxazolidinylene, morpholinylene, octahydroindolylene, octahydroisoindolylene, oxazolidinonylene, oxazolidinylene, oxiranylene, piperazinylene, piperidinylene, 4-piperidonylene, pyrazolidinylene, pyrazolinylene, pyrrolidinylene, pyrrolinylene, quinuclidinylene, tetrahydrofurylene, tetrahydroisoquinolinylene, tetrahydropyranylene, tetrahydrothienylene, thiamorpholinylene, thiazolidinylene, tetrahydroquinolinylene, and 1,3,5-trithianylene.

The terms, arylene, heteroarylene, alkenylenearylene, arylenealkenylene alkenyleneheteroarylene, or heteroarylenealkenylene all refer to divalent forms of aryl, heteroaryl, alkenylaryl, arylalkenyl, alkenylheteroaryl and heteroarylalkenyl radicals.

As used herein, a "hydrogen bond donor" comprises a hydrogen atom attached to an electronegative atom (e.g., fluorine, oxygen, sulfur or nitrogen). In some embodiments, the hydrogen bond donor is —OH, —O($C_{1-6}$ alkyl), —$NH_2$, or —NHOH.

The term "compound," as used herein is meant to include all stereoisomers, geometric isomers, tantomers, and isotopes of the structures depicted, including structures conforming to a generic formula set out herein.

All compounds, and all pharmaceutically acceptable salts thereof, can be either found together with other substances such as water and solvents (e.g., hydrates and solvates) or can be substantially isolated. A compound of the invention or a salt thereof is "substantially isolated" when at least partially or substantially separated from the environment in which it was formed or detected. Partial separation can include, for example, a composition enriched to any extent in a compound of the invention. Substantial separation can include compositions containing at least about 50%, at least about 60%, at least about 70%, at least about 80%, at least about 90%, at least about 95%, at least about 97%, or at least about 99% by weight of a compound or compounds of the invention, or a salt or salts thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" are derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

Synthesis: The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3$^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., 1H or 13C), infrared spectroscopy, spectrophotometry (e.g., UV-visible), mass spectrometry, or by chromatographic methods such as high performance liquid chromatography (HPLC) or thin layer chromatography (TLC).

An exemplary method for preparing certain compounds of the invention is provided in Scheme 1.

Compound 3 was produced by bromination of methyl indole-5-carboxylate, compound 2 (ACC Corporation). Compound 4 is then produced by reacting compound 1 with compound 3. Compound 5 was prepared from the corresponding methyl carboxylic ester, compound 4, by nucleophilic substitution with hydroxylamine in the presence of NaOH and MeOH.

Scheme 1

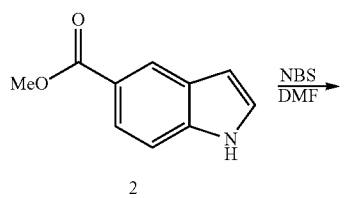

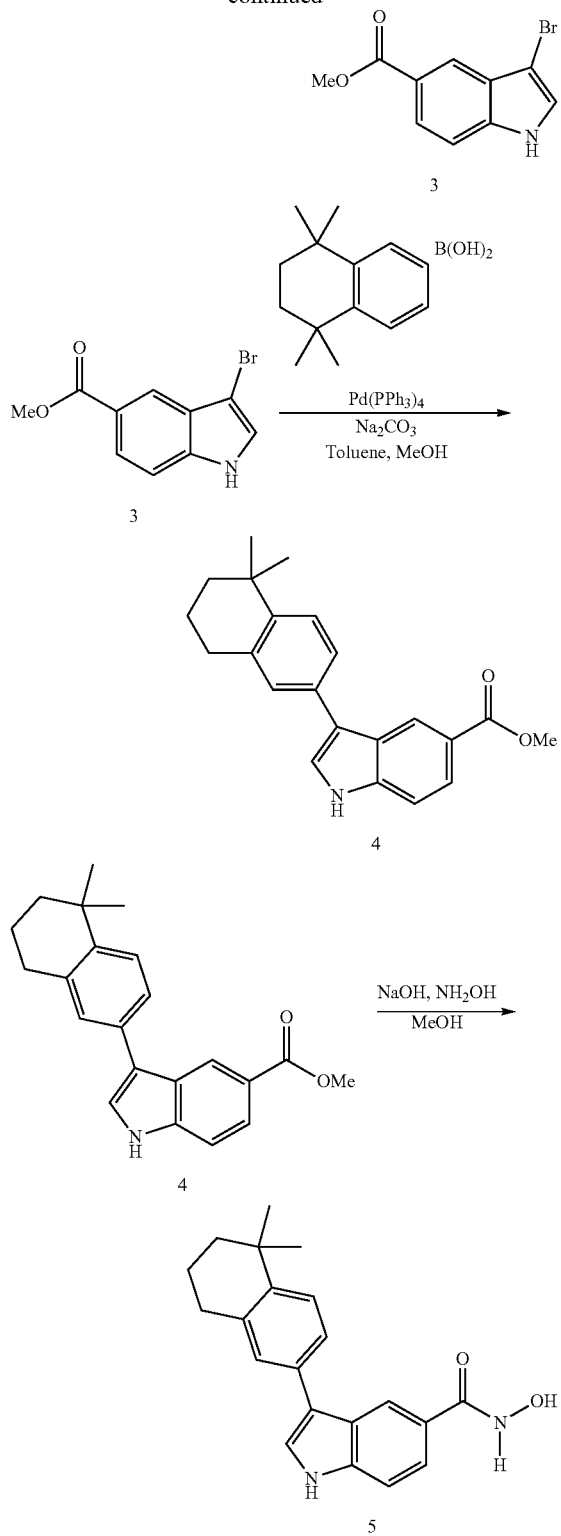

Scheme 2 shows the synthetic scheme for producing compound 8, which was derived from compound 7 by replacement of methyl ester by hydroxamate in the presence of NaOH and MeOH/CH$_2$Cl$_2$. Compound 7 was the product of a Suzuki coupling between compound 1 and methyl 6-bromoquinoline-2-carboxylate, compound 6.

Scheme 2

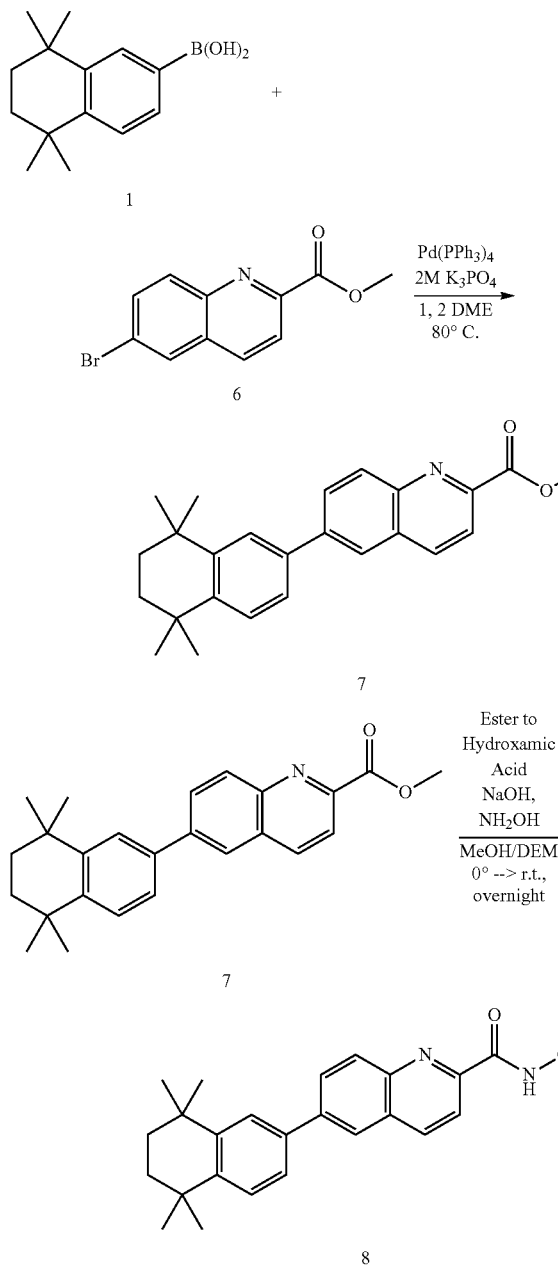

Scheme 3

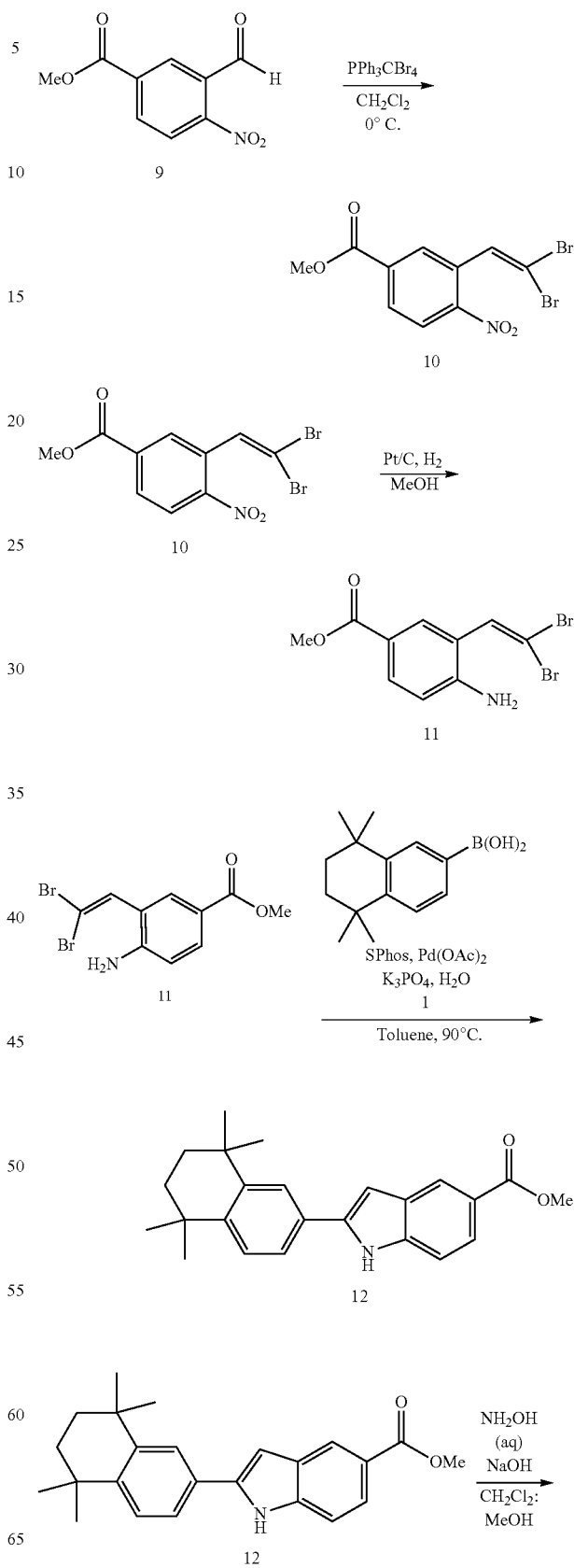

Further, Scheme 3 shows the synthetic scheme for preparing compound 13, which is derived from compound 12 by replacement of the methyl ester by hydroxamate in the presence of NaOH and MeOH/CH₂Cl₂. Compound 12 was prepared by performing concomitant intramolecular Pd(OAc)2-catalysed Buchwald-Hartwig coupling of vinyl bromide and amine in compound 11 followed by intermolecular Suzuki cross coupling of the resulting 2-bromoindole with boronic acid, (5,6,7,8-tetrahydro-5,5,8,8-tetramethyl-2-naphthalenyl) (compound 1). Compound 11 was synthesized from compound 10 by platinium/carbon catalytic hydrogenation of the nitro group. 1,1-Dibromoalkene compound 10 was synthesized by Corey-Fuchs reaction with aldehyde 9.

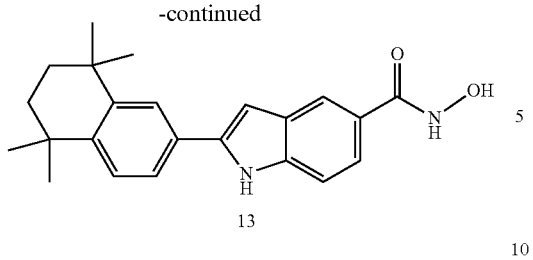
Scheme 4 shows a synthetic method for preparing compound 17.
Scheme 4:
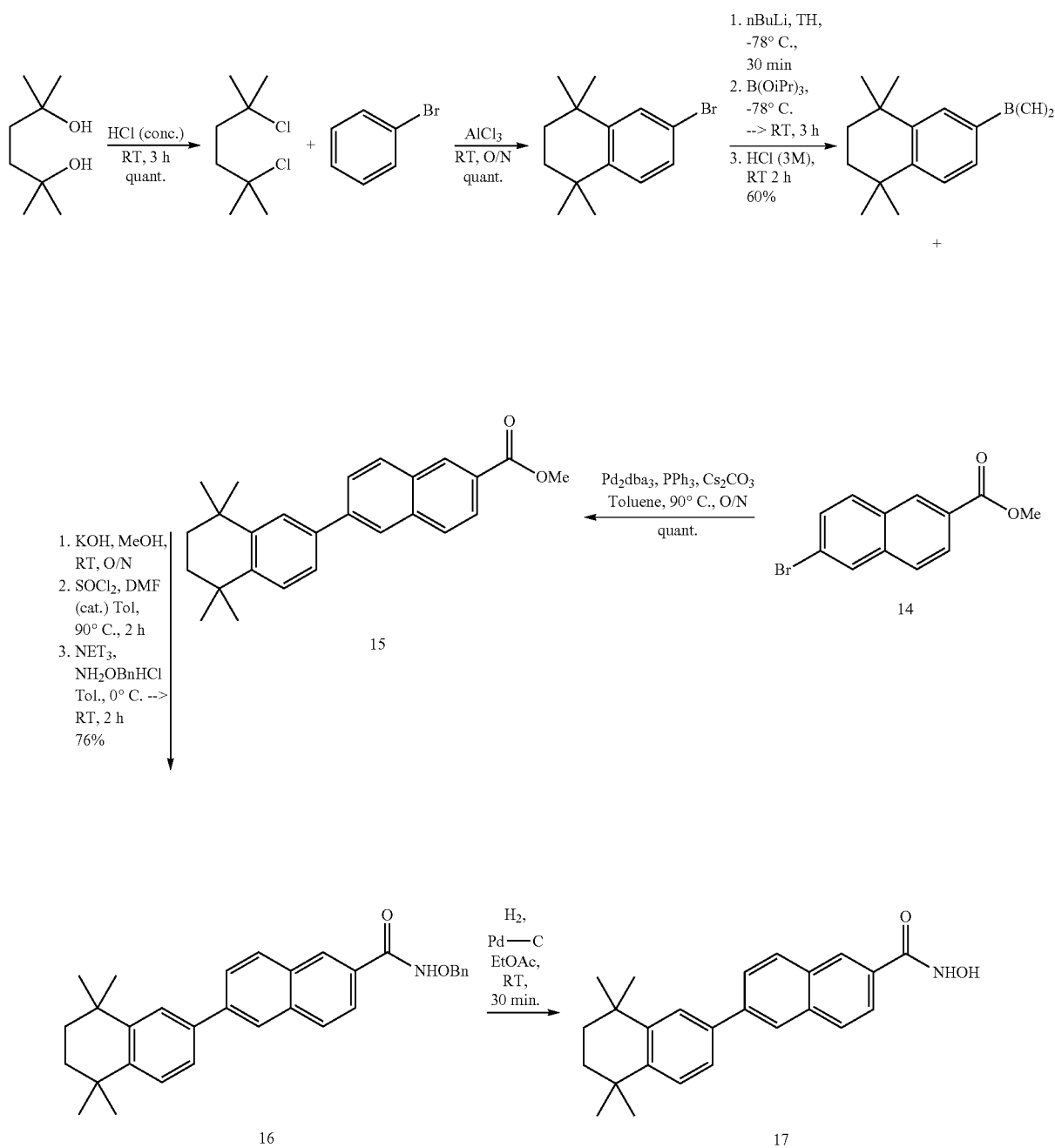

Scheme 5
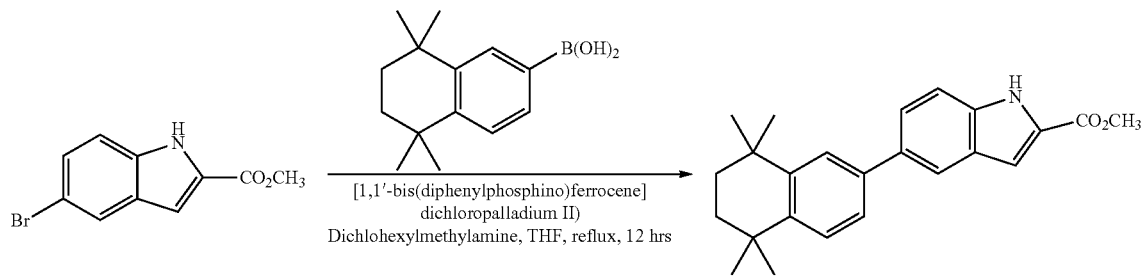
1. KOH, THF/MEOH reflux
2. EDCI, HOBT, 1, 2-phenylenediamine DMF, 12 hrs rt
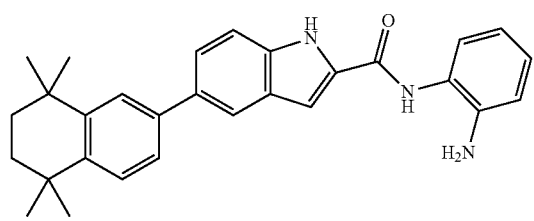
Scheme 6
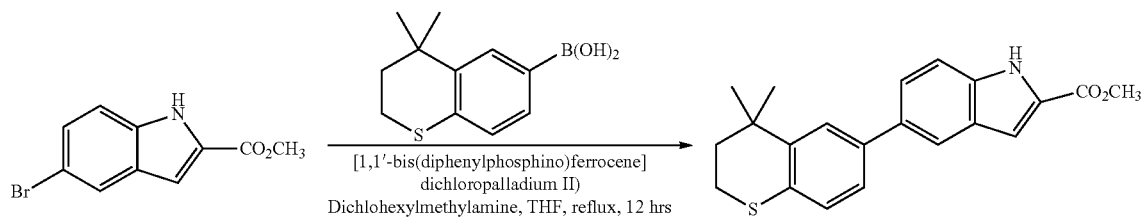
1. KOH, THF/MEOH reflux
2. EDCI, HOBT, phenylenediamine DMF, 12 hrs rt
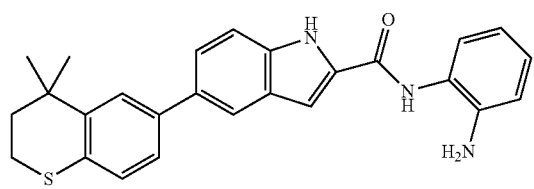

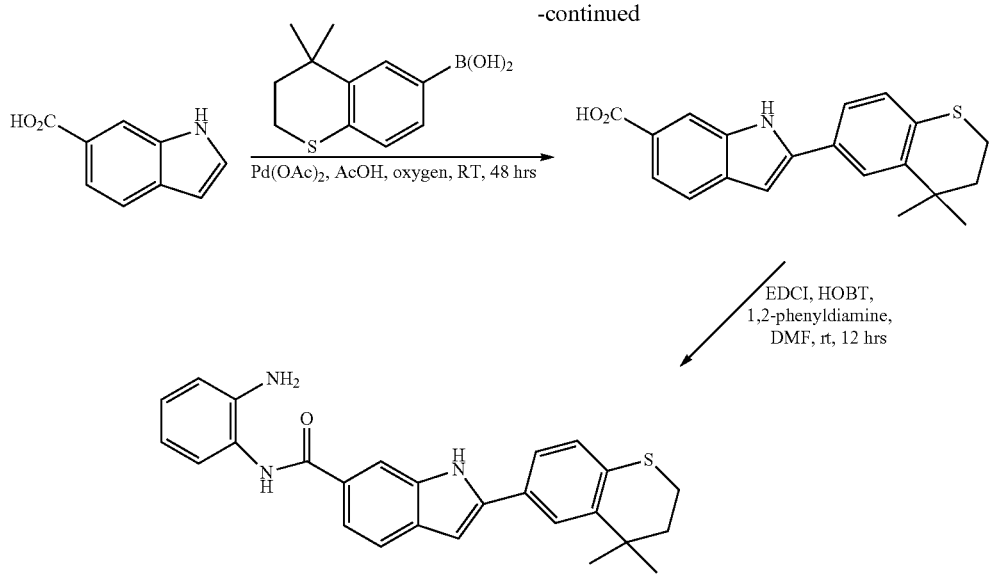

Methods and Use of the present compounds in the preparation of a medicament: In another aspect, the invention features methods of use or methods of treatment for a patient who is suffering from a hyperproliferative disorder (e.g., a cancer, including blood-borne cancers and cancers that manifest as solid tumors). The "use" or methods of use can include the preparation of a medicament or the preparation of a medicament for treating a hyperproliferative disorder, non-malignant tumor, or muscle-related condition as described herein. The medicament(s) can include a compound or compounds as described herein (e.g., for the treatment of a hyperproliferative disorder), and the methods of treating a patient can include a step of administering to the patient a therapeutically effective amount of a compound or compounds as described herein. For ease of reading, we do not repeat the phrase "or a pharmaceutically acceptable salt thereof" at every opportunity. It is to be understood that where a compound of the invention can be used, a pharmaceutically acceptable salt thereof can also be used. In any method of treatment, the method can include a step of identifying a patient in need.

In one aspect, the invention relates to methods of treating a subject who has cancer or a non-malignant tumor, the method comprising administering to the subject a therapeutically effective amount of a compound described herein.

In various embodiments, the use can be directed to, or the methods of treating can be applied to, a subject who has been diagnosed with lung cancer (e.g., a non-small cell lung cancer), a colon cancer, a melanoma, a breast cancer, a renal cancer, an ovarian cancer, a prostate cancer, a cancer of the nervous system (affecting the brain or spinal cord, such as a glioma), a neuroendocrine tumor (e.g., a neuroblastoma), or a blood cancer (e.g., a leukemia or lymphoma).

In one embodiment, the present invention features methods of treating pheochromocytoma in a subject comprising administering to the subject a therapeutically effective amount of a compound of Formula I or a pharmaceutically acceptable salt thereof.

In another embodiment, the invention features methods of treating neuroblastoma in a subject comprising administering to the subject a therapeutically effective amount of compound of Formula I or a pharmaceutically acceptable salt thereof.

As noted, the present invention further provides a compound of Formula I, or a pharmaceutically acceptable salt thereof for use in the preparation of a medicament or for the production of a medicament for use in therapy, including therapy for any condition or type of condition described herein.

Although the invention is not limited to compounds that exert a beneficial effect through any particular mechanism of action, our studies indicate that the compounds of the invention can inhibit tumor growth or survival. Compounds of the invention can also be an effective treatment to reduce metastatic growth of tumors (metastasis).

The present invention further provides methods for treating a disease caused by or associated with the presence of a tumor in a mammalian subject, including identifying a subject in which reduction of tumor mass is desirable, and administering to the subject in need of such treatment a therapeutically effective amount or dose of a compound of the present invention or a pharmaceutical composition thereof. The subject can be a mammal (e.g., a human or veterinary subject). The compound(s) and composition(s) described herein can be administered orally or parenterally. The disease can be a solid extracranial tumor such as, but not limited to, neuroblatoma. The tumor can also be associated with a breast cancer or be an intracranial tumor such, but not limited to, a glioma. As noted, the disease can also be a blood borne cancer such as, but not limited to, leukemia. In some embodiments, the disease is localized to a tissue or organ while in other instances the disease has spread to multiple organs or tissues (e.g., as in metastasis).

As used herein, the term "contacting" refers to the bringing together of indicated moieties (e.g., a compound or composition of the invention) in an in vitro system (e.g., a culture system including muscle cells or precursors or progenitors thereof) or an in vivo system (e.g., within the body, either in the vicinity of or distant from a tumor) in a manner that produces a desired outcome (e.g., a treatment as described herein).

As noted, the present invention also relates to methods inhibiting the loss of muscle mass or muscle function in a subject, and such methods can be carried out by administering to a subject in need thereof a therapeutically effective amount of a compound of Formula I: A-W—Z (I) or a pharmaceutically acceptable salt thereof, where A is

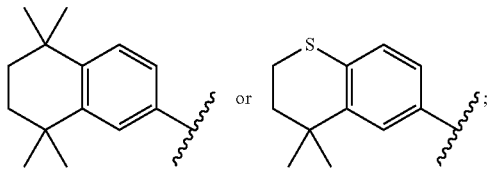 [SMILES: *c1ccc2c(c1)C(C)(C)CCC2(C)C ; *c1ccc2c(c1)C(C)(C)CCS2]

W is a heterocyclylene, arylene, heteroarylene, alkenylenearylene, arylenealkenylene or alkenyleneheteroarylene, heteroarylenealkenylene; and Z is a hydrogen bond donor.

In certain aspects, the loss of muscle mass is associated with an inherited myopathy. in other aspects, the loss of muscle mass is associated with muscular dystrophy, neuromyotonia, nemaline myopathy, multi/minicore myopathy, centronuclear myopathy, mitochondrial myopathy, inflammatory myopathy, metabolic myopathy. In yet another aspect, the loss of muscle mass is associated with intensive care unit-acquired weakness (ICUAW), chronic obstructive pulmonary disease (COPD), heart failure, traumatic injury or malignancy.

The invention also relates to methods for treating myofibers ex vivo. These methods can include the steps of providing an ex vivo preparation of myofibers, optionally comprising a natural or synthetic biological matrix; and contacting the preparation with an amount of a compound of Formula I: A-W—Z (I) or a pharmaceutically acceptable salt thereof, where the amount of the compound is sufficient to promote muscle mass or muscle function and A is

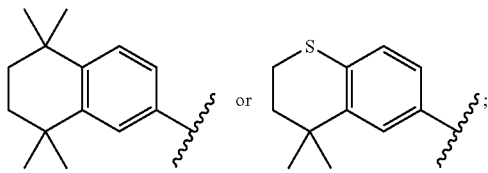 [SMILES: *c1ccc2c(c1)C(C)(C)CCC2(C)C ; *c1ccc2c(c1)C(C)(C)CCS2]

W is a heterocyclylene, arylene, heteroarylene, alkenylenearylene, arylenealkenylene alkenyleneheteroarylene, or heteroarylenealkenylene; and Z is a hydrogen bond donor.

As used herein, the terms "individual" or "patient," or "subject" are used interchangeably (unless the context clearly indicates otherwise) to refer to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (e.g., inhibiting the progression of the disease); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Pharmaceutical Formulations and Dosage Forms: The invention provides compositions (e.g., pharmaceutical compositions) comprising a compound of Formula I or a pharmaceutically acceptable salt thereof and at least one carrier (e.g., a pharmaceutically acceptable carrier). Thus, the invention relates to pharmaceutical compositions comprising a compound as disclosed herein, and a pharmaceutically acceptable carrier. The compound can be present in an amount that confers a clinically beneficial result on a patient to whom the compound has been administered (i.e., a therapeutically effective amount).

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. For example, the compositions may be administered orally or parenterally.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for oral administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, soft and hard gelatin capsules, and sterile packaged powders. In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International Application No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, alimentary oils and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compounds or compositions of the invention contain from about 5 to about 50 mg of the active ingredient. One having ordinary skill in the art will appreciate that this embodies compounds or compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compounds or compositions of the invention contain from about 50 to about 500 mg of the active ingredient. One having ordinary skill in the art will appreciate that this embodies compounds or compositions containing about 50 to about 100, about 100 to about 150, about 150 to about 200, about 200 to about 250, about 250 to about 300, about 350 to about 400, or about 450 to about 500 mg of the active ingredient.

In some embodiments, the compounds or compositions of the invention contain from about 500 to about 1000 mg of the active ingredient. One having ordinary skill in the art will appreciate that this embodies compounds or compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

In some embodiments, the compositions are administered by the oral route for local effect. Solution, suspension, or powder compositions can be administered orally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of a pharmaceutical composition as described herein. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day.

EXAMPLES

Example 1

Synthesis of Compound 21

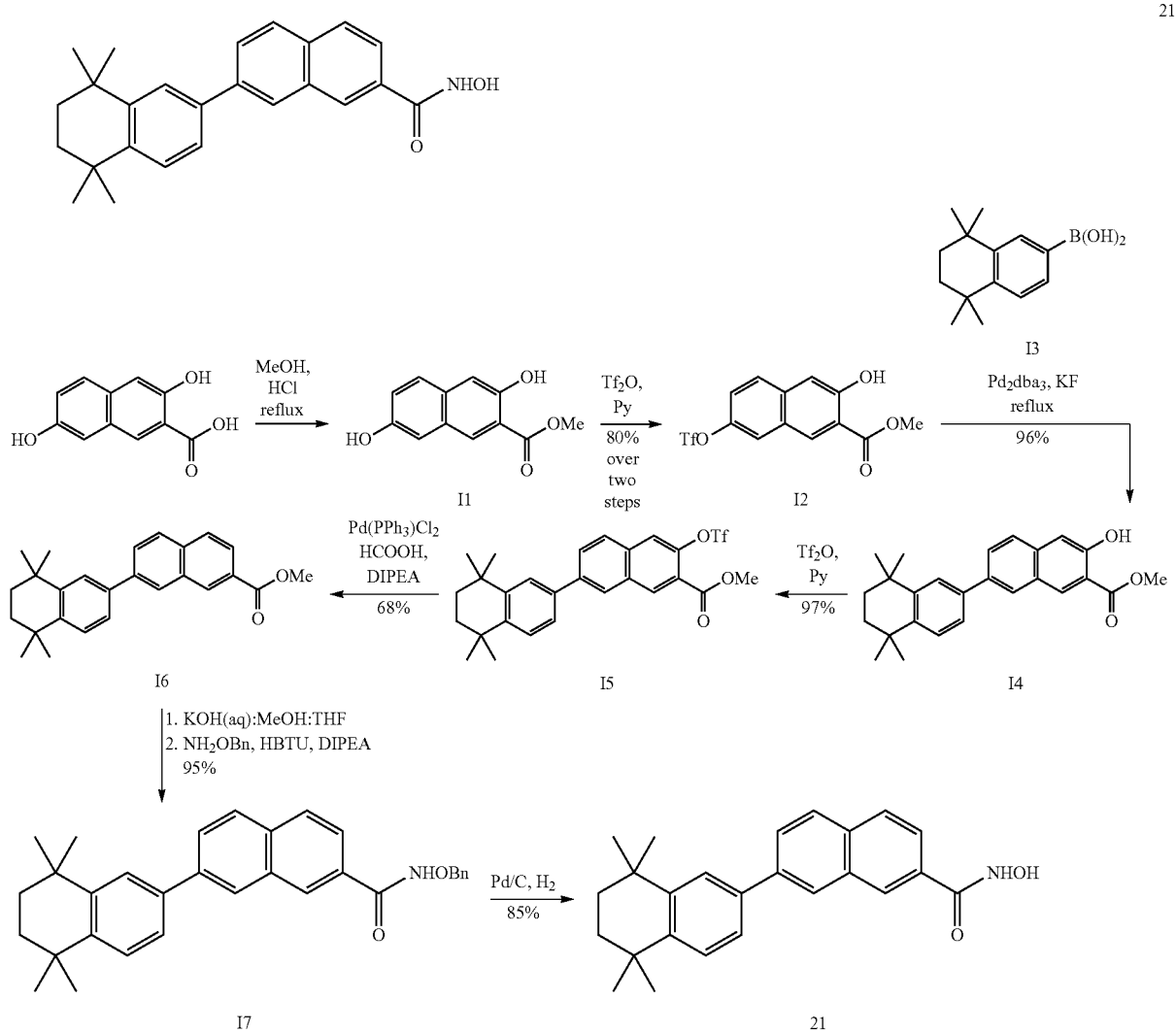

Methyl 3-hydroxy-7-((trifluoromethylsulfonyl)oxy)-2-naphthoate (I1): 3,7-dihydroxy-2-naphthoic acid (200 mg, 0.980 mmol, 1 eq) was dissolved in methanol (5 mL) at room temperature. Concentrated HCl (7 drops, catalytic) was added, and the resulting mixture was stirred at reflux for 16 hours. The reaction mixture was concentrated in vacuo and partitioned between EtOAc (10 mL) and H$_2$O (10 mL). The aqueous layer was further extracted with EtOAc (2×5 mL). The combined organic layer was washed with brine, dried with anhydrous Na$_2$SO$_4$, filtered, and concentrated in vacuo to give the corresponding methyl ester as a yellow solid. No further purification was performed (the crude product was used in the next step).

Characterization data for I1: $\delta_H$ (500 MHz, CDCl$_3$) 4.02 (s, 3H), 7.12-7.17 (m, 2H), 7.27 (s, 1H), 7.60 (d, 1H, J 9 Hz), 10.28 (s, 1H). $\delta_C$ (500 MHz, CDCl$_3$) 52.6, 110.1, 111.8, 114.6, 121.6, 127.8, 128.2, 130.4, 133.4, 151.8, 154.7, 170.3. HRMS (ESI) calculated for C$_{12}$H$_9$O$_4$ (M–H$^+$), 217.0501, found 217.0506.

I1 (214 mg, 0.975 mmol, 1 eq) was dissolved in dry DCM (5 ml). The solution was cooled to 0° C. and pyridine (158 μL, 1.96 mmol, 5 eq) and triflic anhydride (165 μL, 0.975 mmol, 1 eq) were added using syringes in a dropwise manner. The reaction was allowed to warm up to room temperature and stirred for 2 hours. The reaction solution was diluted with Et$_2$O (5 mL) and quenched with excess HCl (aq., 3M). The aqueous layer was further extracted with Et$_2$O (5 mL). The combined organic layer was washed with saturated NaHCO$_3$ and brine, dried with anhydrous Na$_2$SO$_4$, filtered, and concentrated in vacuo to give a brown oil. The crude mixture was purified using flash chromatography (20% EtOAc in hexanes) to give I2 as an off-white solid (262 mg, 80% over 2 steps).

Characterization data for I2: $\delta_H$ (500 MHz, CDCl$_3$) 4.04 (s, 3H), 7.34 (s, 1H), 7.35 (dd, 1H, J 2.5 Hz and 9.5 Hz), 7.69 (d, 1H, J 2.5 Hz), 7.72 (dd, 1H, J 0.5 Hz and 9.5 Hz), 8.49 (d, 1H, J 0.5 Hz), 10.54 (s, 1H). $\delta_C$ (500 MHz, CDCl$_3$) 52.9, 112.1, 115.7, 120.3, 122.8, 126.3, 128.9, 132.4, 136.6, 145.5, 157.3, 169.7. HRMS (ESI) calculated for $C_{13}H_8F_3O_6S$ (M−H+), 358.9994, found 348.9999.

Methyl 6-hydroxy-5',5',8',8'-tetramethyl-5',6',7',8'-tetrahydro-[2,2'-binaphthalene]-7-carboxylate (14): 12 (13.0 mg, 0.0387 mmol, 1 eq) and 13 (27.0 mg, 0.116 mmol, 3 eq) were dissolved in DME (3 mL) at room temperature. PPh$_3$ (2.03 mg, 0.00773 mmol, 20 mol %), KF dihydrate (11.0 mg, 0.116 mmol, 3 eq), and Pd$_2$bda$_3$ (1.77 mg, 0.00193 mmol, 5 mol %) were added to the solution. Distilled water (0.4 mL) was added to the resulting mixture and the reaction was degassed and purged with argon. The reaction mixture was stirred at reflux for 16 hours. After cooling, the reaction mixture was filtered through a layer of Celite and the filtrate partitioned between EtOAc (5 mL) and H$_2$O (5 mL). The aqueous layer was further extracted with EtOAc (5 mL). The combined organic layer was washed with brine, dried with anhydrous Na$_2$SO$_4$, filtered and concentrated in vacuo. The crude mixture was purified using flash chromatography (20% EtOAc in hexanes) to give 14 (14.4 mg, 96%).

Characterization data for 14: $\delta_H$ (300 MHz, CDCl$_3$) 1.34 (s, 6H), 1.37 (s, 6H), 1.74 (s, 2H), 4.04 (s, 3H), 7.33 (s, 1H), 7.43 (m, 2H), 7.61 (s, 1H), 7.76 (m, 2H), 7.97 (s, 2H), 8.56 (s, 1H), 10.45 (s, 1H). $\delta_C$ (500 MHz, CDCl$_3$) 32.3, 32.5, 33.9, 34.1, 34.7, 34.9, 52.9, 125.2, 125.3, 125.6, 125.9, 126.8, 127.4, 128.5, 129.1, 131.2, 131.9, 136.4, 137.7, 141.7, 145.4, 145.7, 168.9.

Methyl 5',5',8',8'-tetramethyl-6-((trifluoromethylsulfonyl)oxy)-5',6',7',8'-tetrahydo-[2,2'-binaphthalene]-7-carboxylate (15): The phenol 14 (20.0 mg, 0.0257 mmol, 1 eq) was dissolved in dry DCM (2 ml). This solution was cooled to 0° C. and pyridine (20.8 μL, 0.129 mmol, 5 eq) and triflic anhydride (13.0 μl, 0.0386 mmol, 1.5 eq) were added using a syringe. The reaction was allowed to warm up to room temperature and stirred for 2 hours. The reaction solution was diluted with Et$_2$O (5 mL) and quenched with excess HCl (aq., 3M). The aqueous layer was further extracted with Et$_2$O (5 mL). The combined organic layer was washed with saturated NaHCO$_3$ and brine, dried with anhydrous Na$_2$SO$_4$, filtered and concentrated in vacuo. The crude mixture was purified using flash chromatography (20% EtOAc in hexanes) to give 15 (13.0 mg, 97%).

Characterization data for 15: $\delta_H$ (300 MHz, CDCl$_3$) 1.35 (s, 6H), 1.38 (s, 6H), 1.75 (s, 4H), 4.03 (s, 3H), 7.47 (s, 2H), 7.63 (s, 1H), 7.76 (s, 1H), 7.95 (s, 2H), 8.14 (s, 1H), 8.72 (s, 1H).

Methyl 5',5',',8'-tetramethyl-5',6',7',8'-tetrahydro-[2,2'-binaphthalene]-7-carboxylate (16): The triflate 15 (29.4 mg, 0.0565 mmol, 1 eq) was dissolved in dry DMF (0.5 mL) at room temperature. DIPEA (29.5 μl, 0.169 mmol, 3 eq), Pd(PPh$_3$)$_2$Cl$_2$ (2 mg, 0.00283 mmol, 5 mol %), and HCOOH (43.0 μL, 0.113 mmol, 2 eq) were added and the final solution was heated to 100° C. for 6 hours. The cooled reaction mixture was filtered through a layer of Celite and partitioned between EtOAc (5 mL) and H$_2$O (5 mL). The aqueous layer was further extracted with another portion of EtOAc (5 mL). The combined organic layer was washed with brine, dried with anhydrous Na$_2$SO$_4$, filtered, and concentrated in vacuo. The crude mixture was purified using flash chromatography (20% EtOAc in hexanes) to give 16 (14.1 mg, 68%).

Characterization data for 16: $\delta_H$ (300 MHz, CDCl$_3$) 1.35 (s, 6H), 1.38 (s, 6H), 1.75 (s, 4H), 4.00 (s, 3H), 7.43 (dd, 2H, Ji 8.1 Hz and 8.1 Hz), 7.65 (s, 1H), 7.84 (m, 3H), 8.04 (d, 1H, J 8.4 Hz), 8.12 (s, 1H), 8.67 (s, 1H).

N-(benzyloxy)-5',5',8',8'-tetramethyl-5',6',7',8'-tetrahydro-[2,2'-binaphthalene]-7-carboxamide (17): To a solution of 16 (14.1 mg, 0.0379 mmol, 1 eq) in dry THF (795 μl) was added methanol (264 μ) and 1M KOH (aqueous, 264 μl, 7 eq). The solution was stirred at room temperature for 15 hours. The reaction mixture was acidified to around pH 3 with 3 M HCl, and extracted with EtOAc (3×5 mL). The combined organic layer was washed with brine, dried with Na$_2$SO$_4$, filtered, and concentrated to dryness to give the corresponding carboxylic acid. The crude acid (18.4 mg, 0.0513 mmol, 1 eq) was then dissolved in dry DMF (2 mL), and OBnNH$_2$ hydrochloride salt (9.01 mg, 0.0564 mmol, 1.1 eq) and DIPEA (26.8 μL, 0.154 mmol, 3 eq) were added to the solution. HBTU (25.3 mg, 0.0667 mmol, 1.3 eq) was added. The resulting mixture was stirred at room temperature for 15 hours. The crude reaction mixture was partitioned between EtOAc and water. The organic layer was washed with brine, dried with Na$_2$SO$_4$, filtered, and concentrated in vacuo. The crude was purified by flash chromatography (6% EtOAc in toluene) to give 17 as a white solid (22.6mg, 95% over 2 steps).

Characterization data for 17: $\delta_H$ (300 MHz, CDCl$_3$) 1.33 (s, 6H), 1.36 (s, 6H), 1.73 (s, 4H), 5.09 (s, 2H,), 7.28 (m, 1H), 7.32-7.38 (m, 5H), 7.61 (d, 1H, J 1.2 Hz), 7.74-7.90 (m, 4H), 8.01 (s, 1H), 8.02 (s, 1H), 8.29 (s, 1H).

N-hydroxy-5',5',8',8'-tetramethyl-5',6',7',8'-tetrahydro-[2,2'-binaphthalene]-7-carboxamide (A): 17 (25.0 mg, 0.0539 mmol) was dissolved in minimal amounts of EtOAc. A catalytic amount of Pd-C was added and the flask was purged with H$_2$ using a balloon. The reaction was further stirred at room temperature in presence of 1atm of H$_2$ gas with TLC monitoring until the starting material was completely consumed (about 20-30 min). The reaction mixture was filtered through a layer of Celite and the filtrate concentrated under reduced pressure to give an orange solid (15 mg, 85% before HPLC purification). The crude product was purified by reverse-phase HPLC (Agilent 1260 Infinity HPLC system equipped with an autosampler, a quaternary pump, a photodiode array detector, and an Agilent Zorbax SB-C18 analytical column, methanol/H$_2$O). The final product A was obtained as a white crystalline solid.

Characterization data for A: $\delta_H$ (300 MHz, CDCl$_3$) 1.35 (s, 6H), 1.38 (s, 6H), 1.75 (s, 4H), 7.43 (d, 1H, J 8.1 Hz), 7.47 (dd, 1H, J 2.1 Hz and 8.7 Hz), 7.64 (d, 1H, J 2.1 Hz), 7.83 (d, 2H, J 8.7 Hz), 7.92 (dd, 2H, J 3.9 Hz and 8,1 Hz), 8.09 (m, 1H), 8.21 (s, 1H), 8.40 (s, 1H). $\delta_C$ (400 MHz, CDCl$_3$) 30.9, 31.2, 33.9, 34.3, 34.9, 35.2, 123.5, 124.4, 124.6, 124.7, 125.3, 126.1, 127.0, 128.5, 129.3, 129.7, 131.9, 135.2, 137.8, 140.7, 144.5, 145.1, 166.9. HRMS (ESI) calculated for $C_{25}H_{26}NO_2$ (M−H+), 372.1969, found 372.1941.

Example 2

Synthesis of Compound B

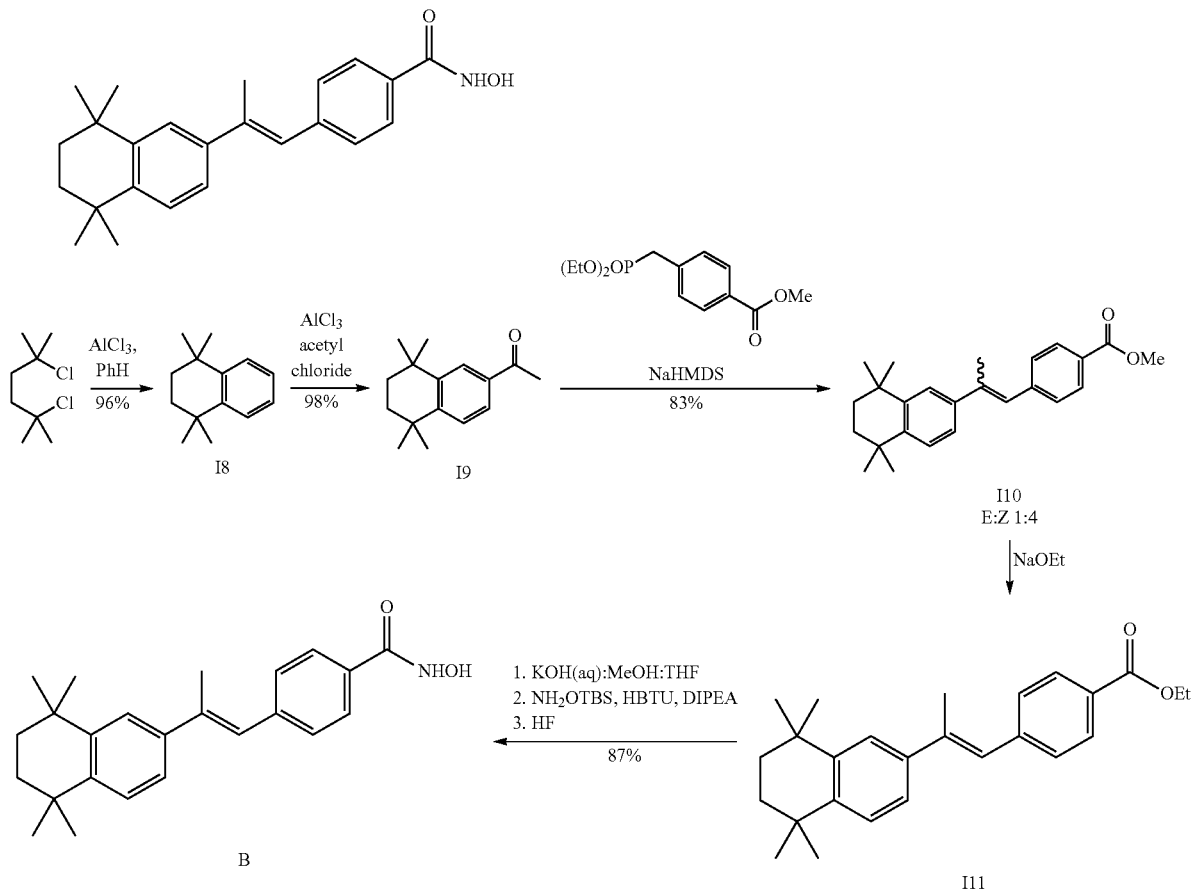

1,1,4,4-tetramethyl-1,2,3,4-tetrahydronaphthalene (I8): 2,5-dichloro-2,5-dimethylhexane (300 mg, 1.64 mmol, 1 eq) was dissolved in dry benzene (25 mL). AlCl$_3$ (22.0 mg, 0.164 mmol, 0.1 eq) was added to the solution, which was stirred at reflux for 16 hours. The reaction was quenched with 3M HCl (5 mL) and extracted with hexanes (10 mL×3). The combined organic layer was washed with brine, dried with Na$_2$SO$_4$, filtered, and concentrated in vacuo. The crude was purified by flash chromatography (100% hexanes) to give 18 (309 mg, 91% yield) as a colourless oil.

Characterization data for 18: $\delta_H$ (500 MHz, CDCl$_3$) 1.33 (s, 12H), 1.74 (s, 4H), 7.16-7.19 (m, 2H), 7.34-7.36 (m, 2H, J 2 Hz and 8.4 Hz). $\delta_C$ (500 MHz, CDCl$_3$) 31.9, 34.2, 35.1, 125.5, 126.5, 144.8.

1-(5,5,8,8-tetramethyl-5,6,7,8-tetrahydronaphthalen-2-yl)ethanone (19): 18 (37.0 mg, 0.197 mmol, 1 eq) was dissolved in dry DCM (5 mL), to which acetyl chloride (15.5 µL, 0.216 mmol, 1.1 eq) and AlCl$_3$ (26.2 mg, 0.216 mmol, 1.1 eq) were added sequentially. The reaction mixture was refluxed for two hours then cooled to room temperature and quenched with water. The crude mixture was extracted with EtOAc (3 mL×3). The combined organic layer was washed with NaHCO3 (saturated, aqueous) and brine, dried with Na$_2$SO$_4$, filtered, and concentrated in vacuo. The crude was purified by flash chromatography (10% EtOAc/hexanes) to give 19 (44.8 mg, 98% yield).

Characterization data for 19: $\delta_H$ (500 MHz, CDCl$_3$) 1.28 (s, 6H), 1.30 (s, 6H), 1.69 (s, 4H), 2.55 (s, 3H), 7.38 (d, 1H, J 8.0 Hz), 7.70 (dd, 1H, J 1.9 Hz and 8.0 Hz), 7.92 (d, 1H, J 1.9 Hz). HRMS (ESI) calculated for C$_{16}$H$_{23}$O (M+H$^+$), 231.1749, found 231.1767.

Ethyl 4-(2-(5,5,8,8-tetramethyl-5,6,7,8-tetrahydronaphthalen-2-yl)prop-1-en-1-yl)benzoate (I12): The Homer Wardsworth Emmons reagent I10 (316 mg, 1.10 mmol, 2 eq) was dissolved in dry THF (5 mL) and cooled to 0° C. NaHMDS (1M solution in THF, 1.10 mL, 2 eq) was added dropwise to the phosphonate reagent and the mixture stirred at low temperature for 30 minutes. I9 (127 mg, 0.552 mmol, 1 eq) was dissolved in dry THF (5 mL) in a separate flask and was slowly added to deprotonated HWE reagent through cannula. The mixture was allowed to slowly warm up to room temperature and stirred until disappearance of starting material. The reaction was quenched with saturated NH$_4$Cl solution and extracted with EtOAc (5 mL×3). The combined organic layer was washed with NaHCO$_3$ (saturated, aqueous) and brine, dried with Na$_2$SO$_4$, filtered, and concentrated in vacuo. The crude product was purified by flash chromatography (20% EtOAc/hexanes) to give I11 as a E:Z mixture (1:4, 166 mg, 83% yield). I11 (166 mg, 0.458 mmol, 1 eq) was dissolved in dry EtOH, to which an excess of freshly prepared NaOEt solution was added. The mixture was stirred at room temperature for two hours. Neutralizing workup and removal of organic solvent yielded I12 as mostly E isomer.

Characterization data for I12 as an E isomer: $\delta_H$ (300 MHz, CDCl$_3$) 1.32 (s, 6H), 1.35 (s, 6H), 1.39 (t, 3H, J 7.1 Hz), 1.72 (s, 4H), 2.30 (d, 3H, J 1.2 Hz), 4.36 (q, 2H, J 7.1 Hz), 6.82 (s, 1H), 7.32 (m, 2H), 7.42 (d, 1H, J 8.1 Hz), 7.47 (d, 1H, J 1.2 Hz), 8.04 (d, 1H, J 8.1 Hz).

(E)-N-hydroxy-4-(2-(5,5,8,8-tetramethyl-5,6,7,8-tetrahydronaphthalen-2-yl)prop-1-en-1-yl)benzamide (B):

I12 (49 mg, 0.135 mmol) was dissolved in THF (1 mL), and KOH (1M, 0.5 mL) and MeOH (0.5 mL) were added. The reaction proceeded at room temperature for 5 hours until the starting material was not observable on TLC. The mixture was acidified with 3M HCl to pH 3 and extracted repeatedly with EtOAc. The combined organic layer was washed with brine, dried with Na$_2$SO$_4$, filtered, and concentrated in vacuo. The crude carboxylic acid was used without purification. The acid was subsequently dissolved in dry DMF (2 mL). NH$_2$OTBS (23.3 mg, 0.158 mmol, 1.1 eq), DIPEA (75.0 μL, 0.430 mmol, 3 eq) were added with stirring at room termperature, followed by HBTU (71 mg, 0.186 mmol, 1.3 eq). The reaction mixture was stirred at room temperature for 16 hours. A quick extraction with EtOAc was performed and the organic layer containing the O-TBS protected hydroxamic acid was concentrated in vacuo and redissolved in DCM (3 mL). An excess of concentrated HF (~20 eq) was added to the DCM solution and the biphasic mixture was stirred vigorously for two hours at room temperature. The reaction was neutralized with saturated NaHCO$_3$ and extracted with additional DCM. The organic layer was washed with brine, dried with Na$_2$SO$_4$, filtered, and concentrated in vacuo. The crude product was purified by reverse-phase flash chromatography (20-95% MeOH in H$_2$O) to yield B as a slightly yellow oil (43 mg, 87%).

Characterization data for B: $\delta_H$ (500 MHz, CD$_3$OD) 1.31 (s, 6H), 1.34 (s, 6H), 1.74 (s, 4H), 2.28 (d, 1H, J 1.5 Hz), 6.82 (s, 1H), 7.02 (dd, 1H, J 2 Hz and 8.5 Hz), 7.31 (m, 2H), 7.45 (d, 2H, J 8.5 Hz), 7.77 (d, 2H, J 8.5 Hz). $\delta_C$ (500 MHz, CD$_3$OD) 30.82, 30.84, 30.9, 33.7, 33.9, 34.8, 35.0, 64.0, 123.1, 123.6, 125.3, 126.2, 126.6 128.7, 128.9, 129.7, 139.5, 140.7, 142.1, 144.0, 144.4, 166.6. HRMS (ESI) calculated for C$_{24}$H$_{28}$NO$_2$, [M−H$^+$] 362.2123, found 362.2132.

Example 3

Synthesis of Compound 20

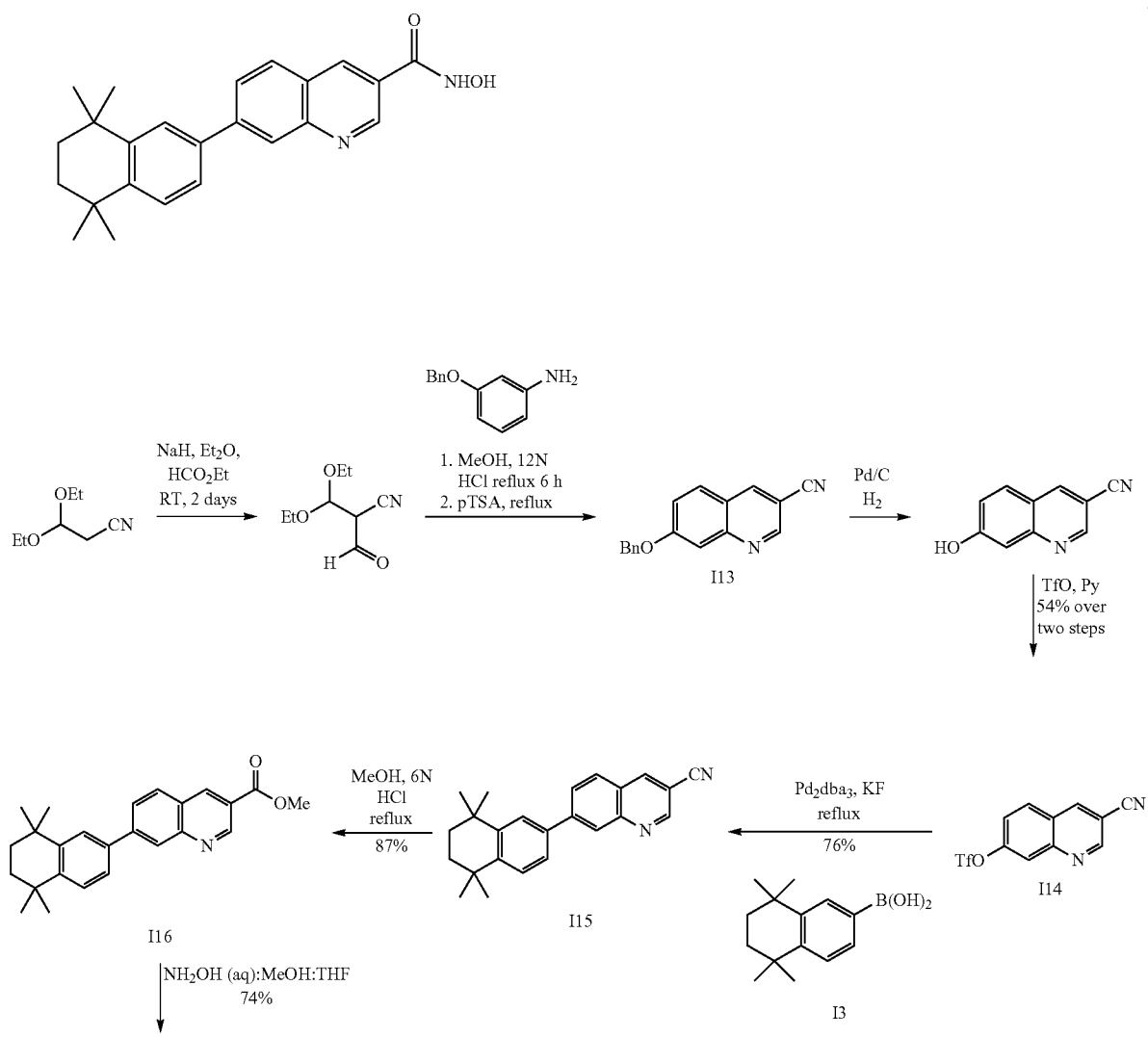

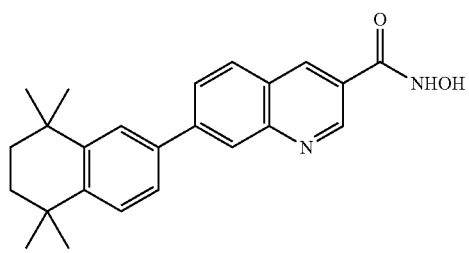

7-(benzyloxy)quinoline-3-carbonitrile (I13): I13 was prepared according to the procedure of Cal T. B., et al, *Journal of Medicinal Chemistry*, 51:1849-1860, 2008.

Characterization data for I13: $\delta_H$ (500 MHz, CDCl$_3$) 5.28 (s, 2H), 7.39-7.51 (m, 5H), 7.65 (dd, 1H, J 2.5 Hz and 9.0 Hz), 8.05 (d, 1H, J 9.0 Hz), 8.14 (d, 1H, J 2.5 Hz), 8.63 (d, 1H, J 2.0 Hz), 9.15 (d, 1H, J 2.0 Hz) $\delta_C$ (500 MHz, CDCl$_3$) 70.6, 116.3, 121.7, 122.3, 122.8, 123.1, 123.3125.4, 127.7, 128.5, 129.5, 130.8, 141.2, 149.1, 151.4.

3-cyanoquinolin-7-yl trifluoromethanesulfonate (I14): I13 (27.0 mg, 0.104 mmol, 1 eq) was dissolved in minimal EtOAc. A catalytic amount of Pd-C was added and the flask was purged with H$_2$ using a balloon. The reaction was further stirred at room temperature in presence of 1 atm of H$_2$ gas with TLC monitoring until the starting material was completely consumed (about three hours). The reaction mixture was filtered through a layer of Celite and the filtrate concentrated under reduced pressure to give an orange oil. The crude product was used in the next step without purification. The crude hydroxyquinoline (17.7 mg, 0.104 mmol, 1 eq) was dissolved in dry DCM (1 mL), pyridine (42.0 µL, 0.519 mmol, 5 eq) and triflic anhydride (27.0 µl, 0.156 mmol, 1.5 eq) were added at room temperature. The mixture was stirred for 2.5 hours at which point the reaction was quenched with water and partitioned between EtOAc and water. The aqueous layer was extracted with additional EtOAc (5 mL×3) and the organic layers combined. The latter was washed with sodium bicarbonate (saturated, aqueous) and brine, dried over anhydrous Na$_2$SO$_4$, filtered and concentrated in vacuo. The purification using flash chromatography (20% EtOAc in hexanes) yielded I14 as a waxy solid (13 mg, 54% over two steps).

Characterization data for I14: $\delta_H$ (500 MHz, CDCl$_3$) 7.64 (dd, 1H, J 2.5 Hz and 9.0 Hz), 8.05 (d, 1H, J 9.0 Hz), 8.14 (d, 1H, J 2.5 Hz), 8.63 (d, 1H, J 2.0 Hz), 9.15 (d, 1H, J 2.0 Hz) $\delta_C$ (500 MHz, CDCl$_3$) 116.3, 117.5, 120.0, 121.7, 122.8, 125.4, 130.8, 141.2, 149.1, 151.4, 151.6.

7-(5,5,8,8-tetramethyl-5,6,7,8-tetrahydronaphthalen-2-yl)quinoline-3-carbonitrile (I15):

I14 (5.7 mg, 0.0189 mmol, 1.0 eq) and I3 (13 mg, 0.0567 mmol, 3.0 eq) were dissolved in DME (1 mL) at room temperature. PPh$_3$ (1.00 mg, 0.00377 mmol, 20 mol %), KF dihydrate (5.30 mg, 0.0567mmol, 3.0 eq), and Pd$_2$bda$_3$ (1.00 mg, 0.000943 mmol, 5 mol %) were added to the solution. Distilled water (10 drops) was added to the resulting mixture and the reaction was degassed and purged with argon. The reaction mixture was stirred at reflux for 16 hours. After cooling, the reaction mixture was filtered through a layer of Celite and the filtrate partitioned between EtOAc (5 mL) and H$_2$O (5 mL). The aqueous layer was further extracted with EtOAc (5 mL). The combined organic layer was washed with brine, dried with anhydrous Na$_2$SO$_4$, filtered and concentrated in vacuo. The crude mixture was purified using flash chromatography (20% EtOAc in hexanes) to give 115 (4.89 mg, 76%).

Characterization data for I15: $\delta_H$ (300 MHz, CDCl$_3$) 1.34 (s, 6H), 1.37 (s, 6H), 1.74 (s, 4H), 7.43 (d, 1H, J 8.1 Hz), 7.51 (dd, 1H, J 2.1 Hz and 8.1 Hz), 7.70 (d, 1H, J 2.1 Hz), 7.83 (bs, 2H), 8.02 (bs, 1H), 8.37 (s, 1H), 8.80 (d, 1H, J 1.5 Hz). $\delta_C$ (300 MHz, CDCl$_3$) 31.9, 34.2, 35.1, 125.5, 126.5, 144.8, 116.3, 117.5, 120.0, 121.7, 122.8, 125.4, 130.8, 141.2, 149.1, 151.4, 151.6.

Methyl 7-(5,5,8,8-tetramethyl-5,6,7,8-tetrahydronaphthalen-2-yl)quinoline-3-carboxylate (I16): I15 (10.0 mg, 0.0294 mmol) was dissolved in MeOH (2 mL) to which concentrated HCl (2 mL) was added. The mixture was heated to reflux with stirring for 16 hours then cooled in an ice bath. The pH was adjusted to neutral with 1M KOH. The reaction mixture was extracted with EtOAc (5 mL×3). The combined organic layer was washed with brine, dried with anhydrous Na$_2$SO$_4$, filtered and concentrated in vacuo. The crude mixture was purified using preperative thin layer chromatography (30% EtOAc in hexanes) to give I16 (9.50 mg, 87%).

Characterization data for I16: $\delta_H$ (300 MHz, CDCl$_3$) 1.34 (s, 6H), 1.37 (s, 6H), 1.74 (s, 4H), 4.03 (s, 3H), 7.46 (d, 1H, J 8.4 Hz), 7.53 (d, 1H, J 8.1 Hz), 7.73 (s, 1H), 7.89 (d, 1H, J 8.1 Hz), 7.98 (d, 1H, J 8.4 Hz), 8.39 (s, 1H), 8.87 (s, 1H), 9.46 (s, 1H).

N-hydroxy-7-(5,5,8,8-tetramethyl-5,6,7,8-tetrahydronaphthalen-2-yl)quinoline-3-carboxamide (C): 116 (9.50 mg, 0.0254 mmol, 1.00 eq) was dissolved in dry THF (2 mL) and cooled in an ice bath. To the solution were added MeOH (0.5 mL) and 50% v/v NH$_2$OH (in water, 0.5 mL, excess). The mixture was allowed to warm up slowly to room temperature and stirred for three days. The pH was adjusted to approximately pH 3 with 1M KOH. The resulting solution was partitioned between water and EtOAc. The aqueous layer was further extracted with EtOAc (5 mL×3). The combined organic layer was washed with brine, dried with anhydrous Na$_2$SO$_4$, filtered and concentrated in vacuo. The crude product was purified by reverse-phase flash chromatography (20-95% MeOH in H$_2$O) to yield C as a clear film (6.5 mg, 74%).

Characterization data for C: $\delta_H$ (300 MHz, CD$_3$OD) 1.32 (s, 6H), 1.37 (s, 6H), 1.77 (s, 4H), 7.48 (d, 1H, J 8.4 Hz), 7.58 (d, 1H, J 8.1 Hz), 7.75 (s, 1H), 7.94 (d, 1H, J 8.1 Hz), 7.98 (d, 1H, J 8.4 Hz), 8.39 (s, 1H), 8.95 (s, 1H), 9.50 (s, 1H). $\delta_C$ (300 MHz, CD$_3$OD) 31.3, 31.4, 34.1, 34.4, 35.2, 35.3, 123.5, 124.3, 124.5, 124.7, 125.20, 126.4, 127.8, 128.6, 128.9, 129.7, 131.6, 136.6, 137.5, 140.7, 148.3, 149.1, 167.9. HRMS (ESI) calcd for C$_{24}$H$_{26}$N$_2$O$_2$, [M−H$^+$] 373.1992, found 373.1978.

Example 4

Synthesis of Compounds 22, 23, and 24

Compound 22

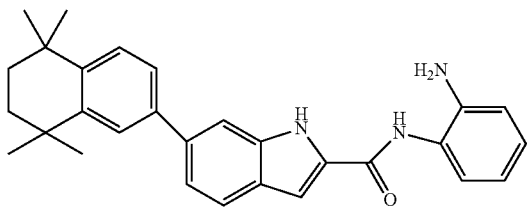

To 200 mg of 6-bromoindole 2-carboxylic acid methyl ester in THF 6 ml was added [1,1'-bis(diphenylphosphino) ferrocene] dichloropalladium(II) (70 mg), dicyclohexylmethylamine (1.2 ml) and boronic acid (300 mg). The mixture was stirred under reflux for 12 hours then cooled to room temperature. The reaction mixture was poured into water and extracted with ethyl acetate, and the resulting organic layer was dried and evaporated. The crude mixture was purified by flash chromatography (ISCO combiflash) using a 10-50% ethyl acetate gradient to afford 200 mg of product, which was dissolved in 10 ml methanol:THF (1:1) and 2 ml of 2N KOH was added to the resulting solution. The solution was heated for 12 hours at 60° C. then cooled to room temperature. Water (50 ml) and 2N HCl (4 ml) was added to the solution, which was then extracted with ethyl acetate (100 ml). The organic layer was dried and evaporated. The crude product was purified by combiflash using 10-100% ethyl acetate gradient to afford the acid as a white solid (140 mg). The acid was dissolved in DMF (5 ml) to which EDCI (140 mg), HOBT (120 mg) and 1,2-phenylenediamine (120 mg) was added and the reaction mixture was stirred overnight at room temperature. The reaction solution was extracted with water (100 ml) and ethyl acetate (100 ml), and the isolated organic layer was dried and evaporated. This crude product was purified using combiflash with 0-100% ethyl acetate to give 70 mg of final product (22).

Characterization data: (300 MHz, CD$_3$COCD$_3$) 10.8 (s, 1H), 9.2 (s, 1H), 7.8 (s, 1H), 7.75 (d, 1H), 7.65 (s, 1H). 7.45-7.5 (m, 5H), 7.1 (m, 1H), 6.9 (m, 1H), 4.7 (bs, 2H), 1.75 (s, 4H), 1.4 (d.6H). MS: [M+1] 438.

Synthesis of Compound 23

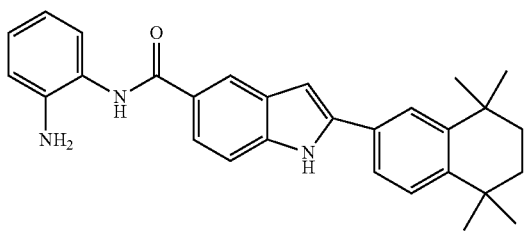 [SMILES: CC1(C)CCC(C)(C)c2cc(-c3cc4cc(C(=O)Nc5ccccc5N)ccc4[nH]3)ccc21]

To 250 mg of indole-5-carboxylic acid was added 16 ml of acetic acid, 300 mg of boronic acid and 70 mg palladium acetate. The reaction was flushed with oxygen, and then stirred for 48 hrs. The solvent was evaporated, and the resulting product purified by flash chromatography (ISCO combiflash) using a 10-50% ethyl acetate/hexane gradient. The purified acid product was dissolved in 5 ml of DMF, and HOBt (150 mg), EDCI (150 mg), and 1,2-phenylenediamine (150 mg) was added to the solution. The reaction was stirred overnight at room temperature. This reaction mixture was poured into water, extracted with ethyl acetate, dried and evaporated. A 5:1 hexane/ethyl acetate solution was added to the crude product, and the suspension was filtered to afford 100 mg of product (23).

Characterization data: NMR (600 MHz, CD$_3$COCD$_3$): 11.7 (s,1H), 9.5 (s,1H), 8.35 (s,1H), 7.8 (s,1H), 7.74 (d,1H), 7.66 (d,1H), 7.47 (d,1H), 7.2 (d,1H), 7.01 (m,2H), 6.8 (d,1H), 6.63 (m,1H), 4.9 (s,2H), 1.66 (s,4H) and 1.3 (d,12H).

Synthesis of Compound 24

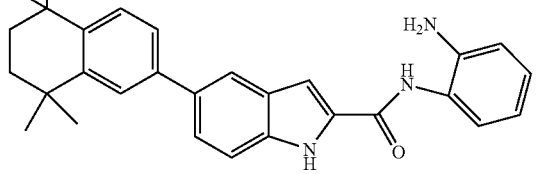

To a solution of 5-bromoindole-2-carboxylic acid methyl ester (250 mg) in THF (6 ml) was added [1,1'-bis(diphenylphosphino)ferrocene]dichloropalladium(II) (70 mg) and boronic acid (300 mg). This reaction mixture was placed degassed with argon and heated at 60° C. for 48 hours. The solvent was evaporated, and the resulting product purified by flash chromatography (ISCO combiflash) using a 10-50% ethyl acetate/hexane gradient. The resulting product (purified ester) was hydrolyzed by heating at 60° C. overnight in a solution of methanol/THF/2N NaOH (1:1:1, 9 ml). This solution was poured into a solution of 5 ml 2N HCl and 50 ml water, and the extracted with ethyl acetate. The organic layer was dried and evaporated. The crude acid (100 mg) was dissolved in DMF (10 ml) to which EDCI (150 mg), HOBt (150 mg) and 1,2-phenylenediamine (150 mg) was added, and this solution was stirred overnight. The solvent was evaporated off, and the resulting product purified by flash chromatography (ISCO combiflash) using a 10-50% ethyl acetate/hexane gradient to provide compound 24.

Characterization data: NMR(600 MHz, CD3SOCD3): 11.6 (s ,1H), 9.75 (s,1H), 7.9 (s,1H), 7.4-7.7 (m,6H), 7.25 (9d,1H), 7.0(m,1H), 6.8 (s,1H), 6.6(s,1H), 4.95 (s,2H), 1.75 (s,4H) and 1.3 (d,12H).

Example 5

The effect of compounds on the enzymatic activity of purified recombinant human HDAC-1, -2, -3, -6, and -8 activity and of purified rat liver HDAC was examined by measuring the deacetylation of synthetic peptides in various preparations of HDACs. HDAC assays were performed using a two-step enzymatic reaction where enzyme activity is correlated to the release of 4-amino-7-methylcoumarin (AMC). AMC fluorescence is measured in a fluorescent plate reading using $\lambda_{ex}$380 nm and $\lambda_{em}$440 nm. The assay was run in a 96-well format using an assay buffer (50 mM Tris-HCl, pH 8, 137 mM NaCl, 2.7 mM KCl, 1 mM MgCl$_2$ and 50 ug/mL ultra-pure, non-acetylated BSA. Purified human recombinant HDAC-1, HDAC-2, HDAC-3/NCOR and HDAC-6 were assayed using Ac-Arg-Gly-Lys (Ac)-AMC (Bachem 4044046) as a substrate. Purified human recombinant HDAC-8 was assayed using Boc-Lys(Tfa)-AMC (Bachem 4060676) as a substrate. Both substrates were used at a final concentration of 10 µM. Final enzyme concentrations in the assays were as follows: 0.38 µg/mL HDAC-2 (Cayman Chem 10009377), 1.37 µg/mL HDAC-6 (Cayman Chem 10009465), HDAC-8 (Cayman Chem 150 µl, diluted 100×), purified rat liver HDAC (Millipore 382165, 0.8 mg/mL proteins diluted 50×).

HDAC-8, HDAC-9, HDAC-10 and HDAC-11 were assayed using HDAC-Glo™ I/II Kit (Promega Corporation G6421) in a total volume of 110 µl following the manufacturer's instructions. Enzyme concentrations were as follows: 230 ng/µL HDAC-8 (Cayman Chem 19380), 100 ng/mL HDAC-9 (Sigma SRP5268), 460 ng/ml HDAC-10 (Axxora/Enzo BML-SE99), 600 ng/mL HDAC- 11 (Axxora/Enzo BML-SE560).

Figure 5A:
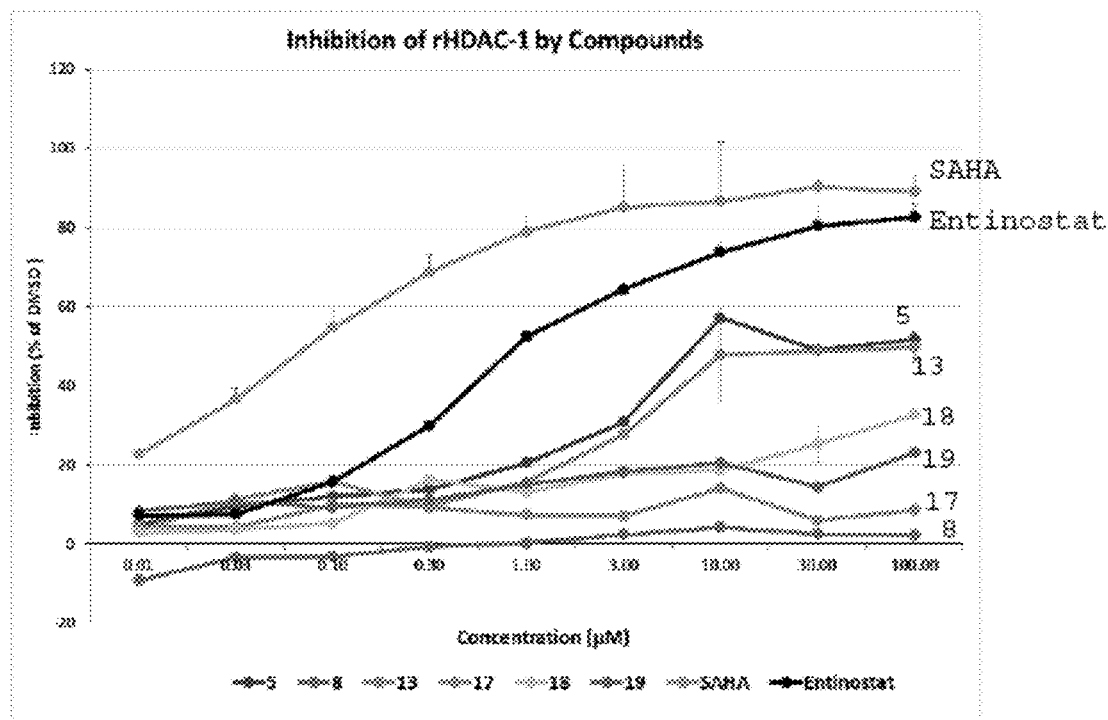
FIG. 5A and FIG. 5B are graphs demonstrating dose-dependent inhibition of recombinant human HDAC-1 and HDAC-6 using compounds disclosed herein.
Figure 5B:
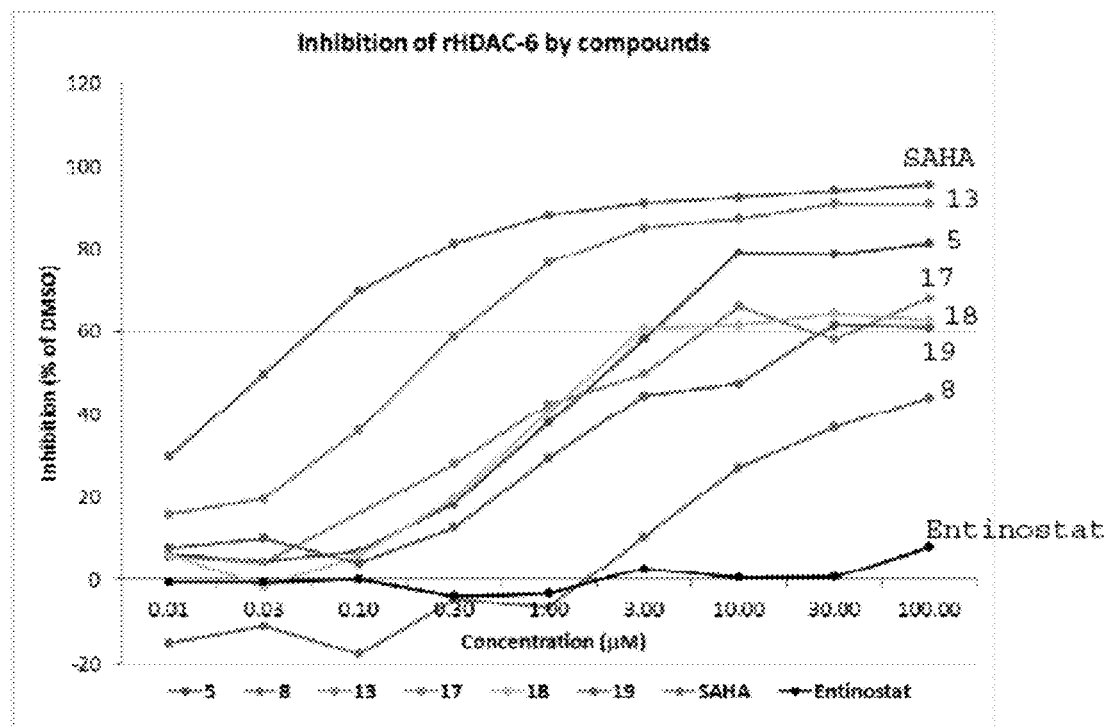

Benchmark compounds, including, entinostat, panabinostat, ricolinostat, romidepsin, and suberoylanilide hydroxamic acid (SAHA) were run alongside the test compounds. The compounds were dissolved in DMSO and tested in duplicate using 1/3 dilution concentration curve. Typically, HDAC preparations were pre-incubated with compounds or DMSO in assay buffer on ice for 5 min prior to substrate addition. The reaction was allowed to proceed for 40 min at 37° C., after which developer solution (0.5% trypsin, 10 µM trichostatin A (TSA)) was added to obtain a final concentration of 0.1% trypsin, 2 µM TSA. After 30 minutes at room temperature, the amount of free fluorogenic AMC was measured as described above. Data showing the effect of various compounds of the invention on HDAC-1 and HDAC-6 are presented in FIGS. 5A and 5B, respectively, and data for all HDACs are summarized in Table 1.

compound 17, and compounds 5 and 13 were six and seventy times more potent than compound 17, respectively (Table 1).

Example 6

The effect of various compounds of the invention on RAR-mediated transcription in MCF7 breast cancer cells was examined by measuring their effect on the transcription of a luciferase reporter gene under the control of a TK promoter placed downstream of a RAR response element. In addition, the effect of the compounds on the closely related RXR-mediated transcription was examined by measuring their effect on the transcription of a luciferase reporter gene under the control of a TK promoter placed downstream of a RXR response element.

Typically, 10,000 cells were plated in 96 wells plates in phenol red-free RPMI medium supplemented with 10% charcoal-stripped Fetal Bovine Serum. After 24 hours, cells were transfected with 0.1 µg of luciferase reporter plasmid and 0.01 µg of a reporter plasmid expressing renilla luciferase (RLuc) gene under the control of a SV40 promoter, using Fugene 6 transfection reagent (0.5 µl/well Promega Corporation). Cells were treated in triplicate with compounds or vehicle (DMSO) for 24 hours. Luciferase and renilla luciferase activities were measured using Dual-Glo reagent (Promega Corporation). Luciferase activity was normalized in each well for renilla activity.

Figure 6A:
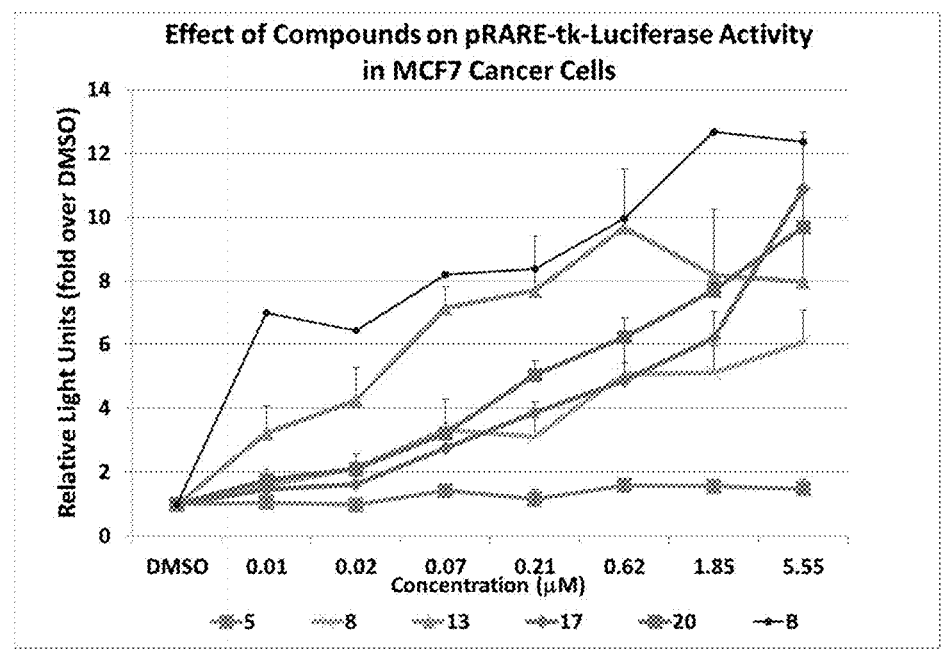
FIG. 6A and FIG. 6B are graphs showing the induction of RAR-dependent transcriptional activity and lack of induction of RXR-dependent transcriptional activity in MCF7 cells.

Results: As shown in FIG. 6A and summarized in Table 2, compounds 8, 13, 18, 19 and 20 activated RARE-dependent

TABLE 1

|  | 1 | 2 | 3 | 6 | 8 | 9 | 10 | 11 | Rat liver | |
| --- | --- | --- | --- | --- | --- | --- | --- | --- | --- | --- |
| 5 | +/− | ++ | ++ | +++ | +++++ | +/− | +/− | +/− | ++ | − |
| 8 | − | − | − | +++ | ++ | − | − | − | ++ | − |
| 3 | +/− | ++ | ++ | ++++ | +++ | +/− | +/− | +/− | +++ | +++ | − |
| 17 | − | − | − | ++ | ++ | − | − | − | − | ++ | − |
| 18 | +/− | ++ | − | +++ | ++ | NT | NT | NT | NT | + | − |
| 19 | − | ++ | − | +++ | − | NT | NT | NT | NT | − | − |
| 20 | − | − | − | ++ | ++ | NT | NT | NT | +/− | +++ | |
| 21 | − | − | − | − | − | − | NT | NT | − | − | − |
| Entinostat | +++ | ++++ | +++ |  | + | +++ | ++ | +++ | NT | − | NT |
| Panobinostat | +++++ | +++++ | +++++ | +++++ | +++++ | +++++ | +++++ | +++++ | NT | − | +++++ |
| Ricolinostat | ++++ | ++++ | +++++ | +++++ | ++++ | NT | ++ | +++ | NT | − | +++ |
| Romidepsin | +/− | +/− | +++ | − | ++ | +++++ | +++ | +++ | NT | − | ++++ |
| SAHA | ++++ | ++++ | +++++ | +++++ | +++++ | +++++ | ++++ | +++ | +++++ | − | +++++ |

Because absolute $IC_{50}$ values vary with different assay systems or substrates, the relative activity of each compound is represented using the symbols "+" or "−". A greater number of "+" signs denotes a greater potency ($IC_{50}$) the inhibition of the respective HDACs. The symbol "+/−" denotes that 100% inhibition of the enzyme could not be reached in the condition used. "NT"=not tested.

Results: Under the experimental conditions, the compounds were mostly inactive active against HDAC-1. However, compounds 5, 13, and 18 inhibited up to ~50% HDAC-1 activity. All of the compounds tested demonstrated an apparent lack of inhibition of HDAC-1, -2, -3, -9, -10 and -11 under the experimental conditions. Surprisingly, compound 5 was shown to be over 200 times more potent than compound 17 in the HDAC-8 inhibition assay. Likewise, compound 13 was shown to be at least 50-fold more potent than compound 17 in the HDAC-6 inhibition assay (FIG. 5A and Table 1), and at least 13-fold more potent than compound 17 in HDAC-8 inhibition assay (Table 1).

Figure 6B:
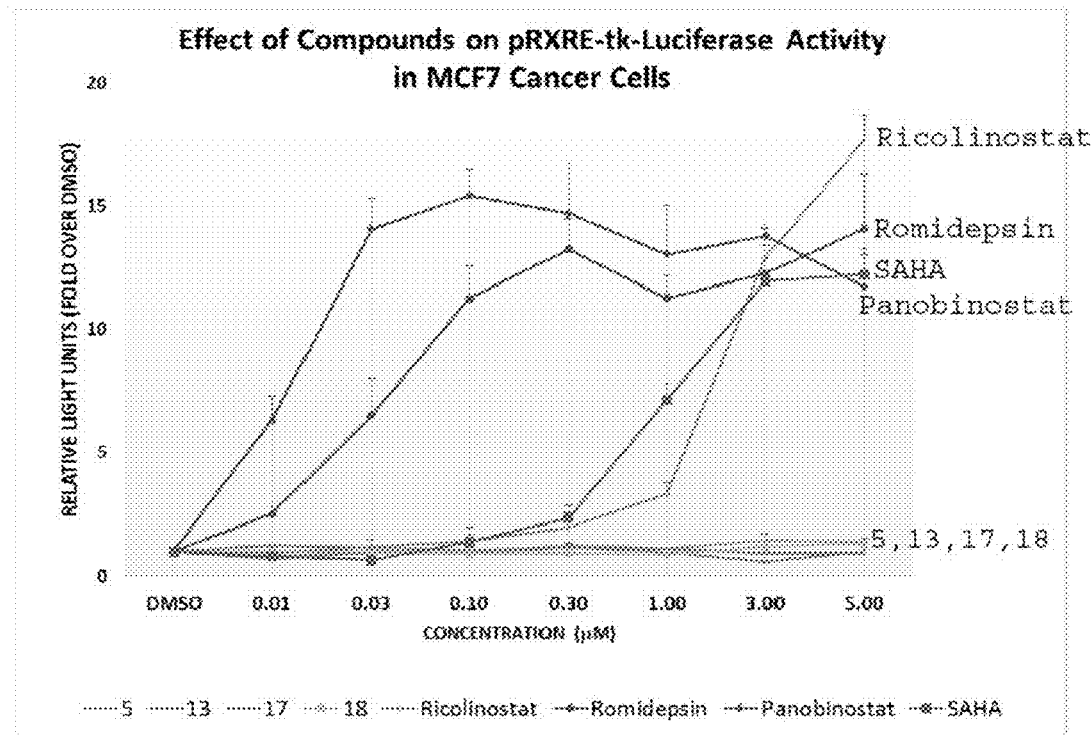

When measuring inhibition of purified rat hepatic HDAC, compound 8 was at least three times more potent than luciferase expression in MCF7 cells. Compound 13 was five to ten times more potent than compound 17 in activating a RARE-tk_luc reporter plasmid transfected in MCF7 cells. Surprisingly, while all benchmark HDAC inhibitors activated transcription from an RXRE-promoter, none of compounds 5, 8, 13, 17, 18, 19, 20 and 21 demonstrated transcriptional activation of RXR (FIG. 6B; Table 2).

TABLE 2

Summary of compounds' ability to activate
RARE-dependent transcription in MCF7 cells

| Compound | RAR | RXR |
| --- | --- | --- |
| 5 | − | |
| 8 | ++ | − |
| 13 | +++ | − |
| 17 | ++ | − |
| 18 | + | − |
| 19 | − | − |
| 20 | +++ | |

TABLE 2-continued

Summary of compounds' ability to activate
RARE-dependent transcription in MCF7 cells

| Compound | RAR | RXR |
|---|---|---|
| 21 | − | − |
| Entinostat | − | NT |
| Panobinostat | − | +++++ |
| Ricolinostat | − | +++ |
| Romidepsin | − | ++++ |
| SAHA | − | +++++ |

Example 7

The cytotoxicity of compounds was examined and directly compared to compound 17, by measuring cell survival of clonal tumor cell lines IMR-32, BE2C (neuroblastoma), as well as MDA-MB-231, BT20, HCC-38 (Basal) and MCF7 (luminal) breast cancer cells (ATCC). Cells were cultured in phenol red-free RPMI medium supplemented with 10% FBS and 1 mM Ala-Glu. Typically, 10,000-20,000 cells/well were plated in a 96 well plate (Costar 3197). Cells were exposed to compounds or vehicle (1% DMSO final). Cells were maintained in the presence of compound for four or five days. Media and compounds were renewed every 48 hours. Cell survival was measured using the luminescence CellTiterGlo kit (Promega Corporation) and expressed as relative light unit as fold over DMSO.

Figure 7A:
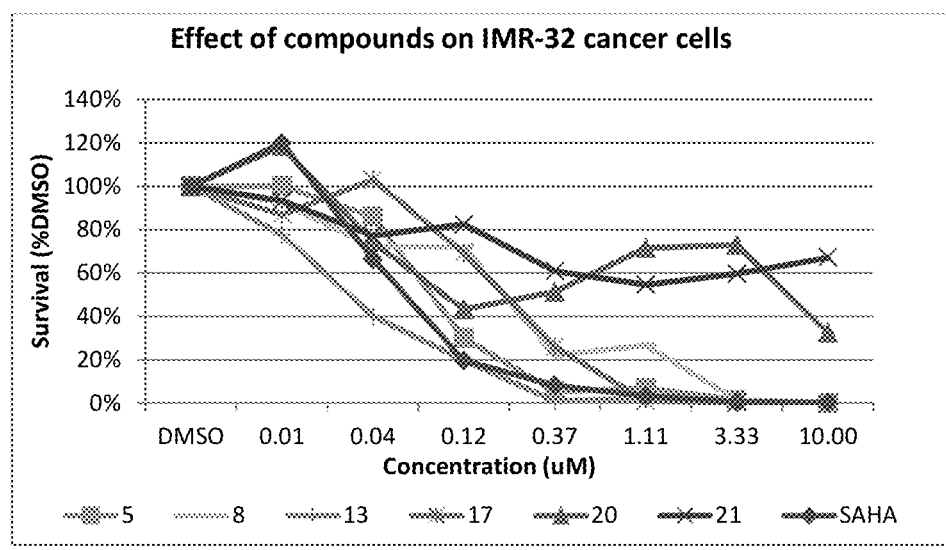
FIG. 7A, FIG. 7B and FIG. 7C are graphs depicting the cytotoxic effect of compounds disclosed herein in high risk neuroblastoma (IMR-32 and BE-2C) and triple negative breast cancer (MDA-MB-231) cell lines.
Figure 7B:
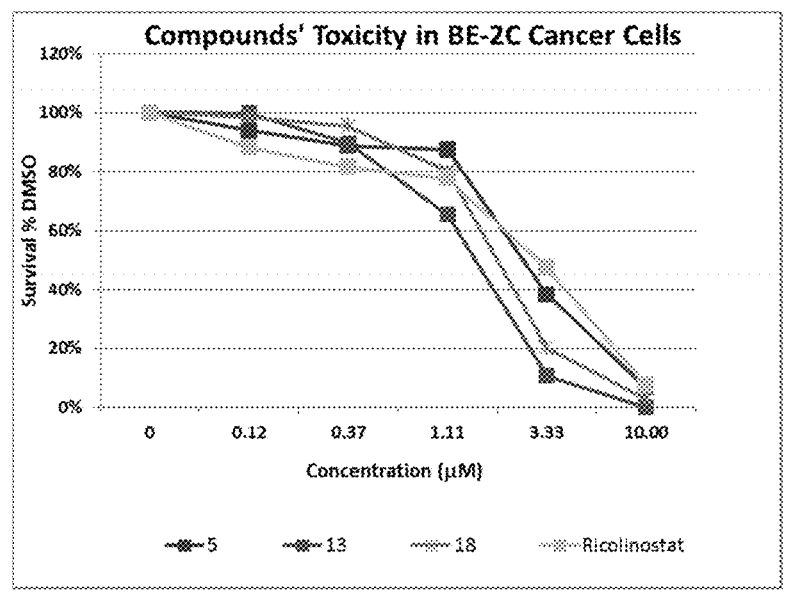
Figure 7C:
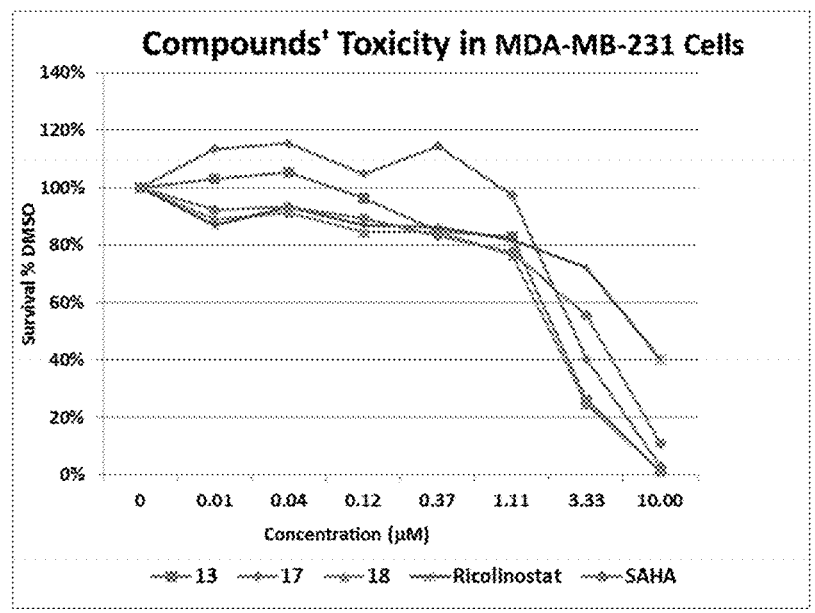

Results: The data show that compounds were cytotoxic in a variety of cancer cell lines (FIGS. 7A-C). In IMR-32 neuroblastoma cells, the compounds tested were cytotoxic in the 30 nM to 300 nM range. Strikingly, compounds 5 and 13 were ten-fold more potent than compounds 17 and 8 in killing IMR-32 cells (FIG. 7A). Strikingly, in both BE-2C and MDA-MB-231 cancer cell lines, compounds 13 and 18 were more potent than compound 17, SAHA or Ricolinistat (FIGS. 7B-7C).

Example 8

The effect of certain compounds on intracellular acetylation of target proteins was tested in high risk neuroblastoma cells, BE-2C and IMR-32 cells.

BE-2C cells were grown to confluence in phenol-red-free RPMI media supplemented with 10% FBS and 2.5 mM Ala-Glu. The cells were treated with DMSO or 5 μM compound 13, Ricolinostat (2 uM), SAHA (2 uM), or TSA (1 uM), in DMSO for 16 hours. Total and Lys 40 acetylated alpha tubulin were detected using specific antibodies.

IMR32 cells were grown to confluence in phenol-red-free RPMI media supplemented with 10% es grade FBS and 2.5 mM Ala-Glu. Cells were treated with DMSO or 1 μM or 5 μM compound 13 in DMSO for 16 hours. Protein extracts were prepared in RIPA buffer in the presence of protease and phosphatase inhibitors. Proteins were separated on a 4-20% gel by PAGE and transferred to a nitrocellulose membrane. Beta actin, total and Lys382 acetylated p53, and Lys40 acetylated alpha, and total tubulin were detected using antibodies (Cell Signaling #8557, #2524 #2525, #12152 and #2144 respectively) using manufacturer recommended conditions.

Figure 8:
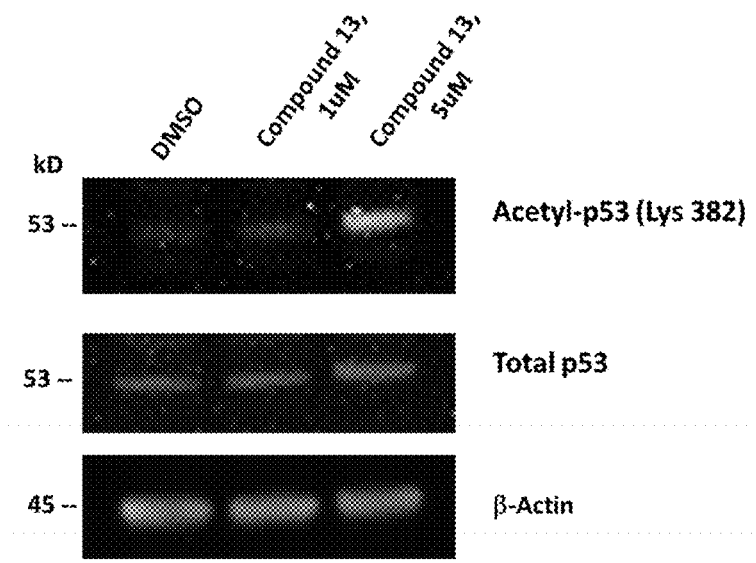
FIG. 8 is a series of gels showing the effect of compound 13 on intracellular acetylation of p53 protein in IMR-32 neuroblastoma cells.
Figure 9:
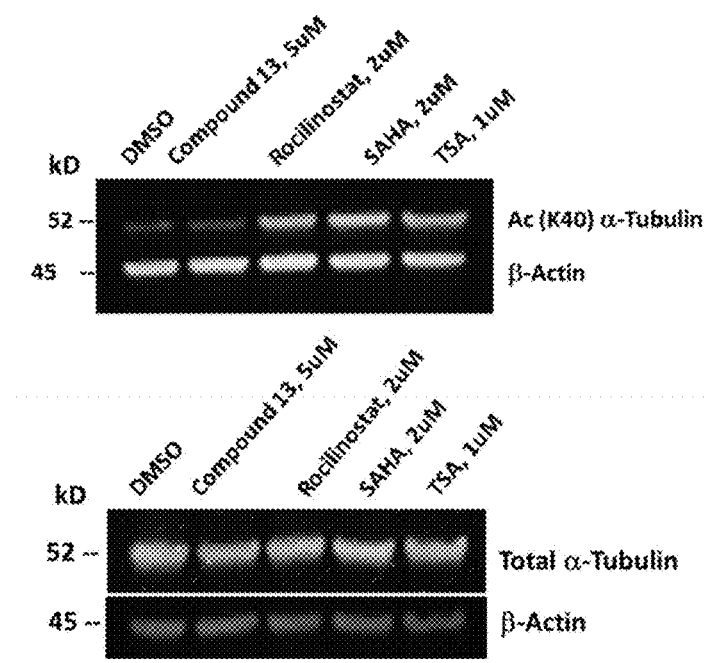
FIG. 9 shows a series of gels demonstrating the effect of certain compound on intracellular acetylation of alpha-tubulin in BE-2C neuroblastoma cells.

Results: The data show that, consistent with the HDAC inhibitory activity observed in vitro (Table 1), under conditions where neither the level of total p53 nor that of total beta actin were affected, addition of 1 μM or 5 μM compound 13 resulted in a pronounced accumulation of lysine acetylated p53 (FIG. 8). Surprisingly, while treatment with ricolinostat, SAHA and TSA all resulted in a pronounced Lysin (K) 40 alpha-Tubulin acetylation, no significant acetylation was observed in compound 13-treated cells at 5 μM, a concentration greater than $IC_{50}$ (FIG. 9). The lack of increased alpha tubulin acetylation was confirmed using LC-MS analysis. These findings confirm that compound 13 acts as a bona fide inhibitor of HDAC activity, and suggests that the cytotoxicity of this compound does not result from tubulin acetylation.

Example 9

The effect of compounds on myoblast fusion was examined in C2Cl2 cells maintained in RPMI media supplemented with 2% horse serum. C2Cl2 myoblastic cells where purchased from the American Type Culture Collection (ATCC) and maintained undifferentiated in RPMI media (Corning) supplemented with 2 mM L-Alanine-L-Glutamine (ATCC) and 1 mM pyruvate (Corning). Undifferentiated cells where maintained below 70% confluence. For long term cultures and compound treatment, cells where plated at high density CellBIND Culture Dishes (corning 3294, 3296, 3337) and in RPMI supplemented with 2% Horse Serum (Gibco) and 2 mM L-Alanine-L-Glutamine (ATCC) and 1mM pyruvate (Corning). Compounds were dissolved in DMSO at 1000 time the final concentration and diluted 1-in-1000 in the media covering the cells. Media and compounds were changed daily. For immunocytochemistry, cells were fixed in 2% PFA in HBSS for 10 minutes and left in HBSS at 4° under humidified atmosphere and processed for immunocytochemistry. For myosin heavy chain detection (MHC), cells were first incubated in 100 ul -1 ml 0.15 M Glycine in DPBS for 10 minutes, rinse with DPBS. 100 ul-1 ml 0.5% Triton-X in DPBS was added for 10 minutes, rinsed with DPBS, and followed by incubation with 100 ul blocking agent (10% goat serum in DPBS) for 30 min at room temperature. MF20 primary antibody in 10% goat serum in DPBS was added at 1/60 dilution for 30 min at room temperature and rinsed three times with 100 ul DPBS. IgG2b goat anti mouse secondary antibody (Jackson Immuno-Research) was added at 1:1000 in 10% goat serum in DPBS for exactly 30 min at room temperature then rinsed 3 times with 100 ul DPBS. A final rinse in $H_2O$ was performed and cells were covered with two drops of Elvanol and cover gently with cover slip and allowed to dry in the dark for 24-48 hours.

Figure 10:
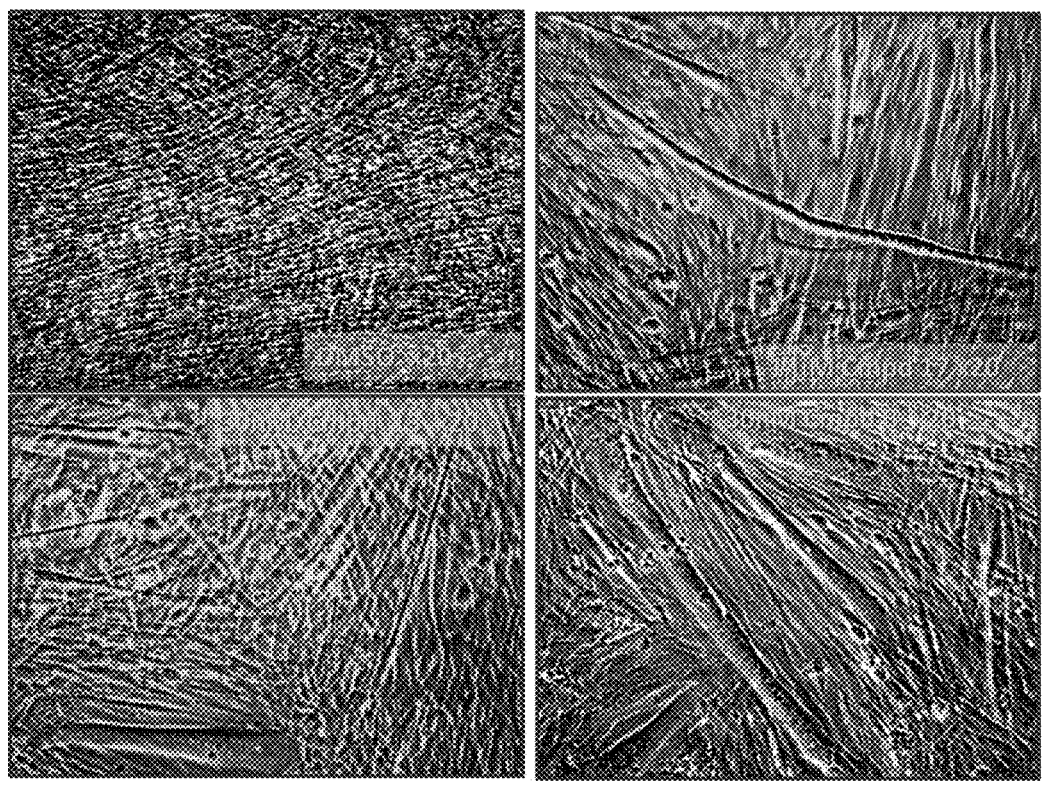
FIG. 10 is a series of photomicrographs showing immunohistochemically stained C2C12 cells in culture and the effect of certain compounds on fiber apparition and maintenance in long term culture.
Figure 11:
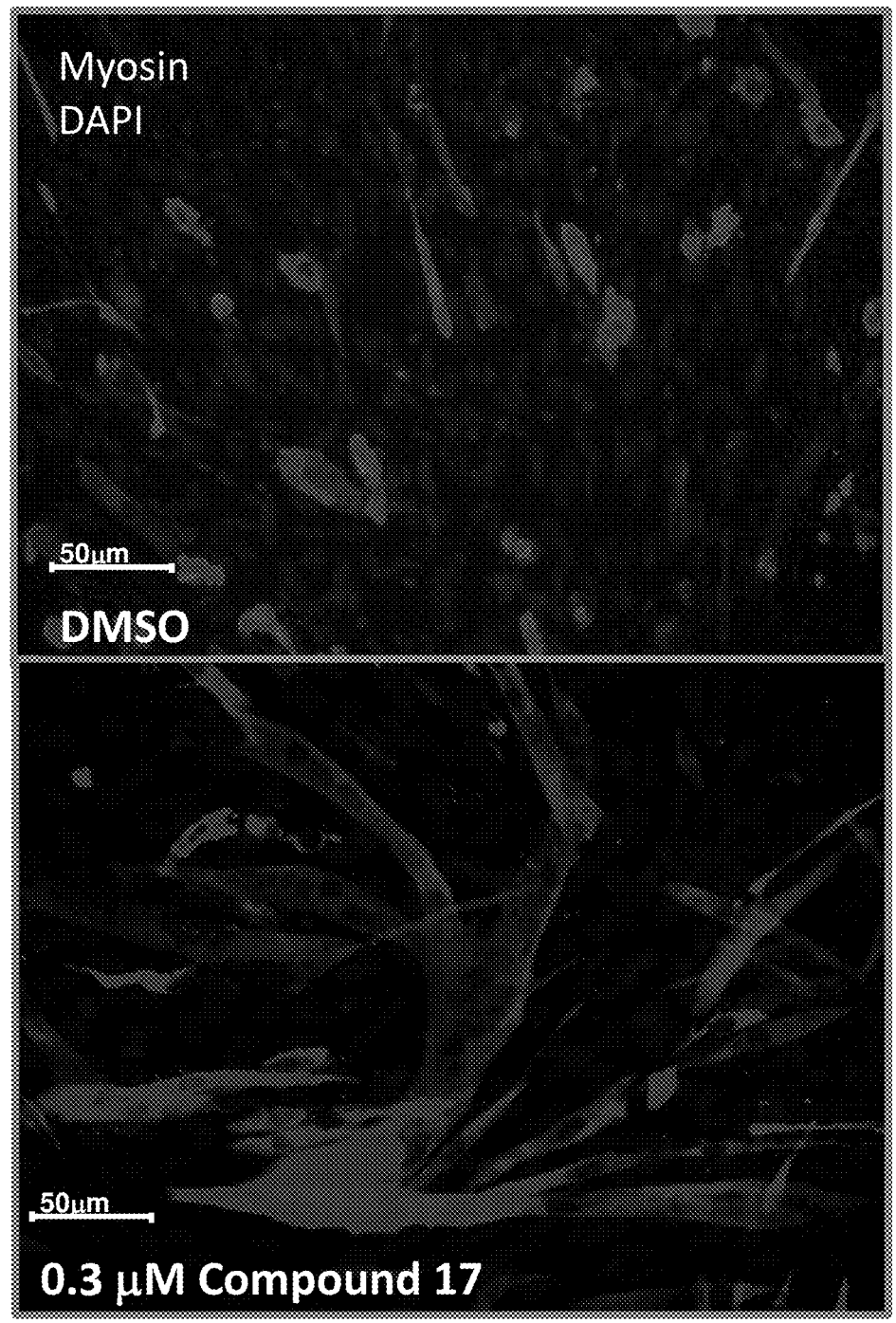
FIG. 11 shows how the certain compounds of the invention affect fusion of differentiated mononuclear C2C12 myoblasts in long term cultures.

Results: Surprisingly, our data suggest that under long-term cultures in suboptimal
RPMI-containing media, addition of compounds 13, 17 or B enhances the fusion of single cells into large multinucleated, elongated C2Cl2 myotubes (FIG. 10). Immunohistochemistry staining assays suggest that the compounds promote the fusion and/or maintenance of myosin heavy chain (MHC)-expressing differentiated myoblasts. In DMSO-treated C2Cl2 cells cultured for 10 days, myotube formation does not occurs despite the presence of a large number of almost exclusively mononucleated MHC-expressing differentiated myoblasts with a single polynucleated-MHC-expressing myotube. Under the same conditions, using 300 nM of compound 17 resulted in the majority of MHC-expressing cells being polynucleated myotubes with an average of 5-10 nuclei per cell, suggesting that fusion was promoted (FIG. 11).

Figure 12A:
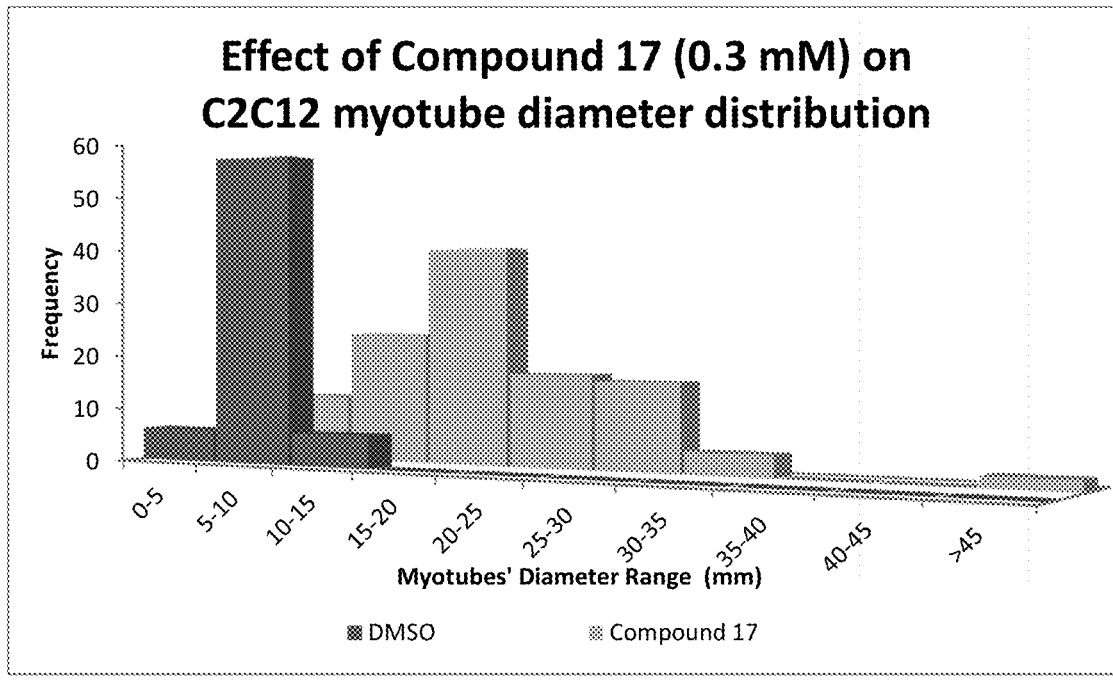
FIG. 12A and FIG. 12B are bar graphs showing the effect of compound 17 on the distribution of the length and diameter of myotubes in long term C2C12 culture.
Figure 12B:
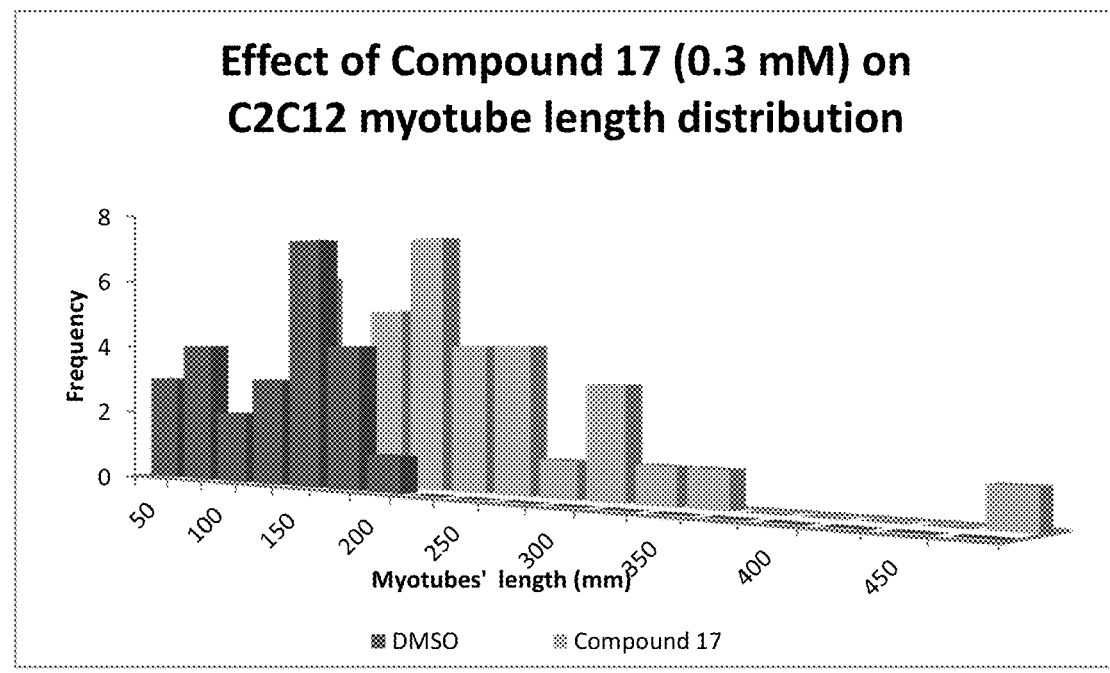

The quantitation of the average distribution of myotubes' length and diameter demonstrate that in the presence of 300 nM of compound 17 are longer and larger than when treated with DMSO (FIGS. 12A and 12B).

Taken together, our data suggest that the compounds tested significantly improve myoblast fusion and/or myotube survival in long-term cultures.

Example 10

C2Cl2 myoblasts were seeded at 100,000 in 30 mm plate in growth medium (Phenol red-free RMPI containing 10%

FBS, Sodium pyruvate and Ala-Glu), and "pre-treated" with DMSO or 200 nM of compounds 13 or 17. At confluence cells were shifted to differentiation media (high glucose DMEM, +0.2% HS+1× Insulin/Transferrin/Selenium (Life Tech 41400-045)+Glutamine, without Pyruvate). Fully differentiated C2Cl2-derived myotubes were left in culture without media renewal for 8 days followed by media renewal and microscopic examination.

Figure 13:
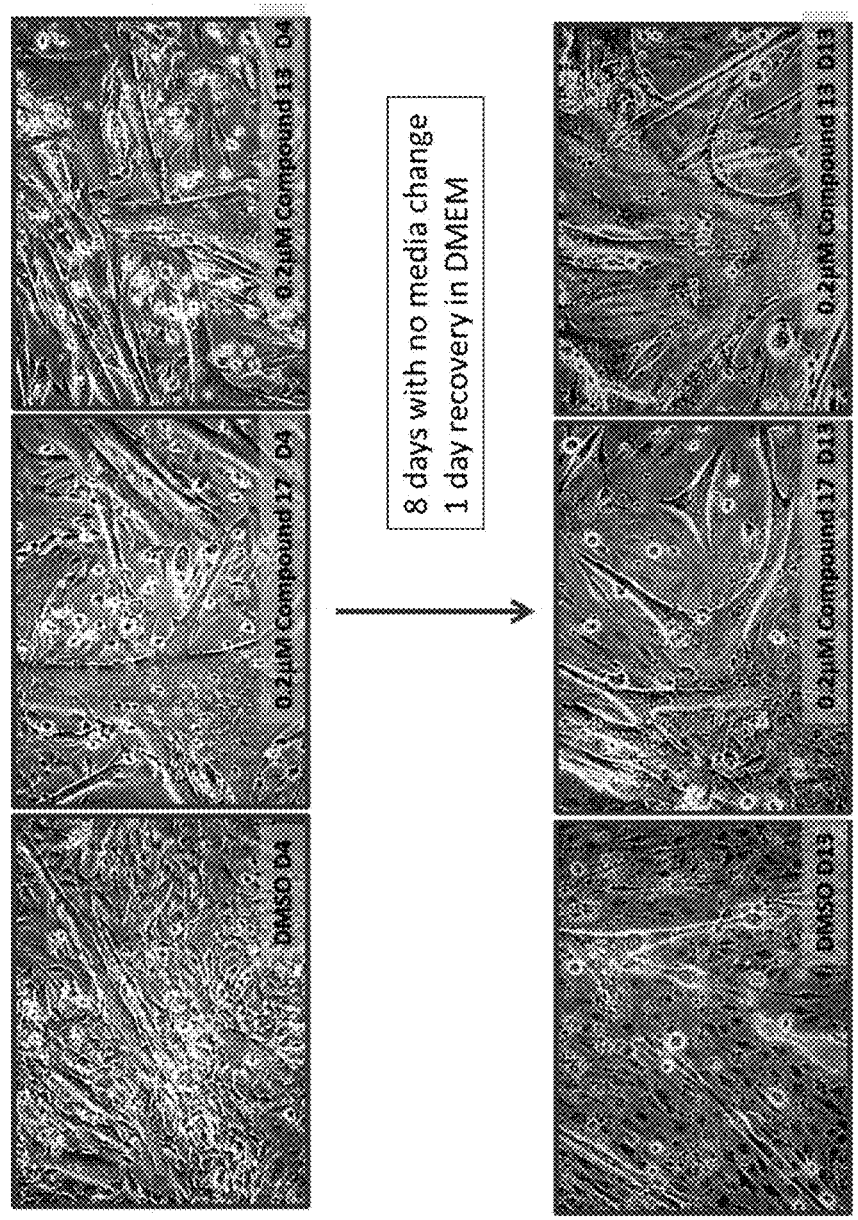
FIG. 13 shows the effect of certain compounds on myotube degeneration in differentiated C2C12 cells.

Results: The data show that extensive cellular fusion was observed after 72 hours differentiation in cells that were treated with compounds 13 or 17 versus DMSO (FIG. 13 top).

In addition, when left in exhausted media for over 8 days, DMSO-treated myotubes, but not myotubes treated with compounds 13 or 17, underwent severe structural atrophy and cell death. In contrast, myotubes treated with compounds 13 or 17 withstood culture stress conditions with very little structural alteration (FIG. 13 bottom).

Example 11

Figure 14A:
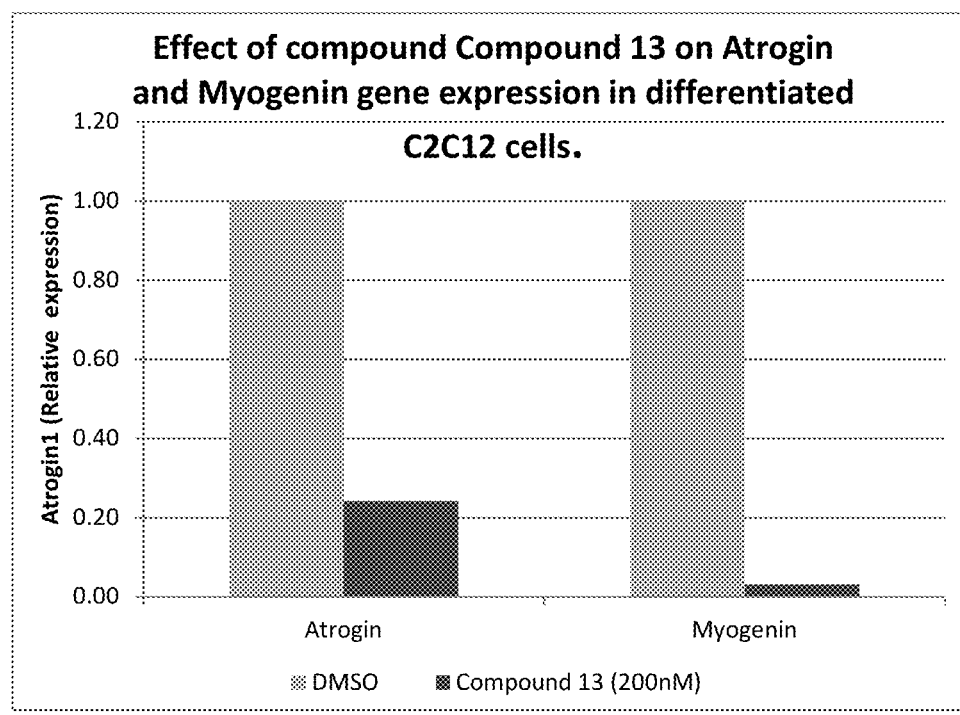
FIG. 14A and FIG. 14B are bar graphs showing the effect of compounds 13 and 17 on myofiber gene expression in C2C12 cells.
Figure 14B:
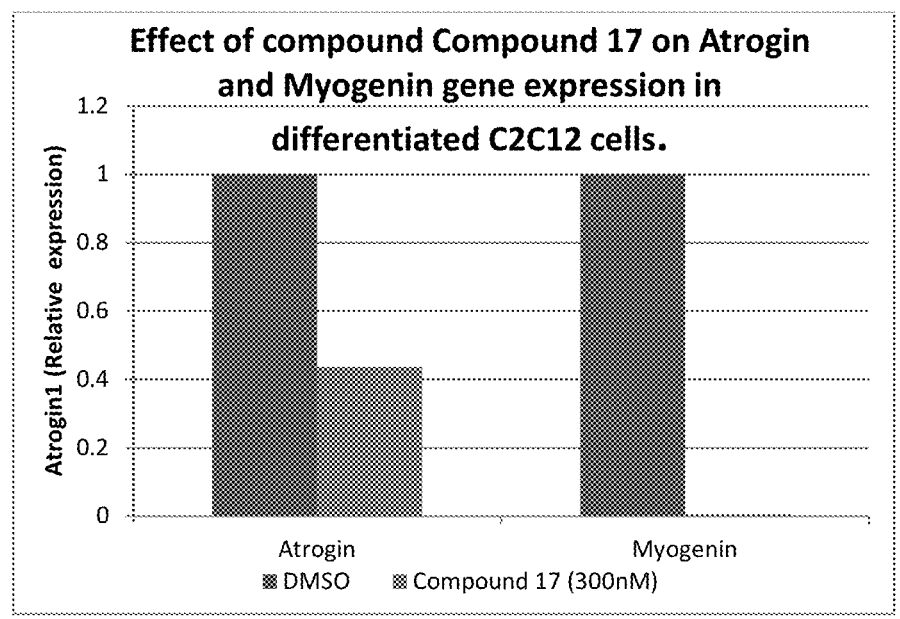

Treatment with compounds 13 or 17 downregulates the expression muscle-atrophy genes myogenin and Atrogin in long term C2Cl2 cultures (FIGS. 14A and 14B).

Quantitative RT-PCR was performed on RNA prepared from cell treated as in Example 9. At day 10 of the experiment, cells were rinsed in HBSS (without calcium or magnesium) and RNA was prepared using FastLane Cell cDNA Kit (Qiagen). Quantitative PCR was performed using Eppendorf and SYBR amplification mix (Sigma-Aldrich) using the gene specific primer combination given in Table 3. Data were normalized for ribosomal housekeeping gene RPLPO Results: Consistent with a role in preserving myotube integrity during long term cultures, compounds 13 and 17 down-regulated the expression of genes implicated in myofiber degradation.

TABLE 3

Sequence of gene-specific primers used in Q-RT PCR quantitation of myofiber-degradation associated genes.

| | ATROGIN | MYOGENIN | RPLP0 |
|---|---|---|---|
| Forward Primer | CTTCTCAGAGAGGCAGATTC (SEQ ID NO: 3) | CCCAACCCAGGAGATCAT (SEQ ID NO: 4) | CGGAGGAATCAGATGAGGATA (SEQ ID NO: 5) |
| Reverse Primer | TCTTCTTGGGTAACATCGTACA (SEQ ID NO: 6) | CTGGGAAGGCAACAGACATACAGAC (SEQ ID NO: 1) | CGGAGTTTTAAGAGAAG (SEQ ID NO: 2) |

Example 11

Mouse pharmacokinetics studies were conducted in female athymic nude or male

C57/B6 mice (n=3). Due to its very poor aqueous solubility, compound 17 was formulated in 66% PEG-400/33% H2O-1% Tween-80. In contrast compound 13 was formulated in 66% PEG-400/33% H2O. Compounds were administered PO (30 mg/kg) or IV (5mg/kg), and plasma concentrations were measured by UV/HPLC. The results are presented in FIG. 15 and pharmacokinetic parameters for each compounds are summarized in Table 4.

TABLE 4

| | Compound 17 | Compound 13 |
|---|---|---|
| $AUC_{0-\infty}$ (µM*h) | 28.71 | 42.00 |
| $C_{max}$ (µM) | 2.08 | 5.54 |
| $T_{max}$ (h) | 4.3 | 1.4 |
| F (%) | 19.7 | ~40 |
| CLp(mL/min/kg) | 10.2 | 0.24 |
| Vd, ss (L/kg) | 4.6 | 8 |
| MRT (h) | 7.1 | 6.9 |

Figure 15:
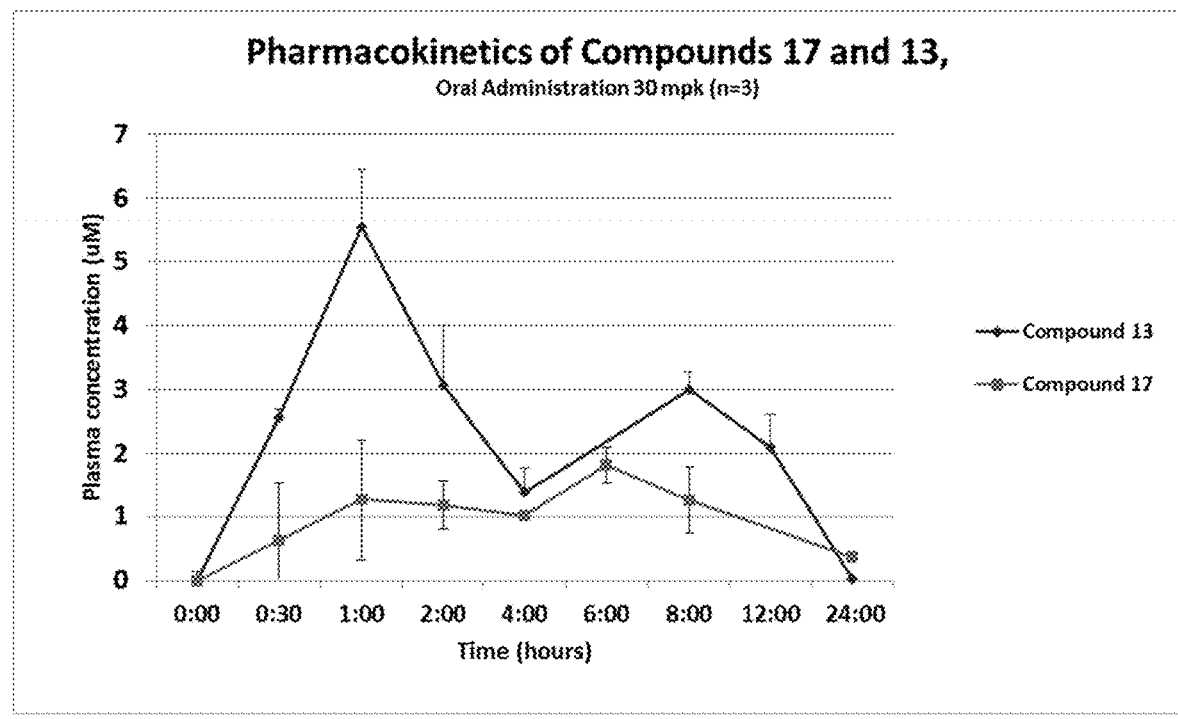
FIG. 15 is a graph comparing the pharmacokinetic profile for compounds 13 and 17.

Results: Compound 13 displayed improved aqueous solubility and pharmacokinetics properties compared with compound 17. Notably, oral bioavailability, AUC, Cmax were markedly higher for compound 13, while T max was markedly reduced (FIG. 15 and Table 4).

The invention claimed is:

1. A method of treating a subject who has cancer or a non-malignant tumor, the method comprising administering to the subject a therapeutically effective amount of a compound of Formula I, a pharmaceutically acceptable salt thereof, or a composition comprising said compound, wherein Formula I is:

A-W—Z                                                        (I)

wherein A is

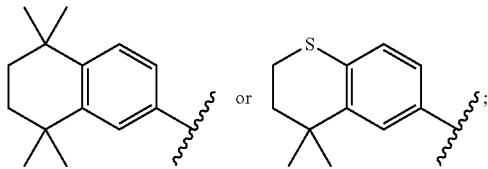 [SMILES: *c1ccc2c(c1)C(C)(C)CCC2(C)C ; *c1ccc2c(c1)C(C)(C)CCS2]

W is a heterocyclylene, arylene, heteroarylene, alkenylenearylene, arylenealkenylene alkenyleneheteroarylene, or heteroarylenealkenylene; and
Z is a hydrogen bond donor, with the proviso that the compound is not

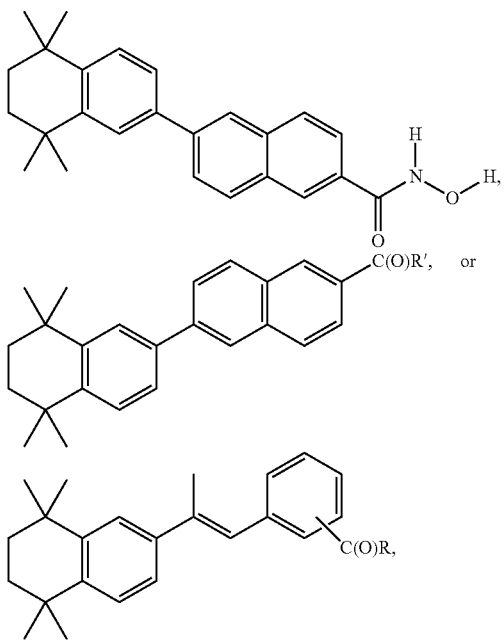

where R is —OH, —OCH₃ and —NHOH; and R' is —OH or —OCH₃.

2. The method of claim 1, wherein W is an indolinylene linked to A at any one of positions 2, 3, 4, 5, 6 or 7 of the indolinylene; a quinolinene linked to A at any one of positions 2, 3, 4, 5, 6, 7, or 8; or an isoquinolinene linked to A at any one of positions 1, 3, 4, 5, 6, 7, or 8.

3. The method of claim 1, wherein W is -propylenephenylene-.

4. The method of claim 1, wherein Z is —C(O)NR¹R² or —C(O)OR³, wherein R¹ and R² are each independently hydrogen (H), hydroxyl (OH), C₁₋₆ alkyl, hydroxyC₁₋₆ alkyl, aminoC₁₋₆ alkyl, or aminoaryl; and R³ is H or C₁₋₆ alkyl.

5. The method of claim 2, wherein Z is linked to the indolinylene, quinolinene, or isoquinolinene at any one of the positions that is not linked to A.

6. The method of claim 4, wherein W is

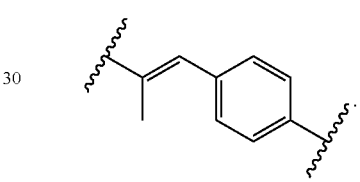

7. The method of claim 1, wherein W is an indolinylene linked to A at any one of positions 2, 3, 4, 5, 6 or 7 of the indolinylene; Z is —C(O)NR¹R² or —C(O)OR³, wherein R¹ and R² are each independently hydrogen, hydroxyl, C₁₋₆ alkyl, hydroxyC₁₋₆ alkyl, aminoC₁₋₆ alkyl, or aminoaryl; and R³ is H or C₁₋₆ alkyl, and wherein Z is linked to the indolinylene at any one of positions 2, 3, 4, 5, 6 or 7 of the indolinylene not linked to A.

8. The method of claim 1, wherein W is a quinolinene linked to A at any one of positions 2, 3, 4, 5, 6, 7 or 8 of the quinolinene; Z is —C(O)NR¹R² or —C(O)OR³, wherein R¹ and R² are each independently hydrogen, hydroxyl, C₁₋₆ alkyl, hydroxyC₁₋₆ alkyl, aminoC₁₋₆ alkyl, or aminoaryl; and R³ is H or C₁₋₆ alkyl, and wherein Z is linked to the quinolinene at any one of positions 2, 3, 4, 5, 6, 7 or 8 of the quinolinene.

9. The method of claim 1, W is a isoquinolinene linked to A at one of positions 1, 3, 4, 5, 6, 7 or 8 of the isoquinolinene moiety; Z is —C(O)NR¹R² or —C(O)OR³, wherein R¹ and R² are each independently hydrogen, hydroxyl, C₁₋₆ alkyl, hydroxyC₁₋₆ alkyl, aminoC₁₋₆ alkyl, or aminoaryl; and R³ is H or C₁₋₆ alkyl, and wherein Z is linked to the quinoline ring at any one of positions 2, 3, 4, 5, 6, 7 or 8 of the isoquinolinene.

10. The method of claim 7, wherein Z is —C(O)NR¹R²; R¹ is H; and R² is OH.

11. The method of claim 7, wherein Z is —C(O)NR¹R²; R¹ is H; and R² is aminoaryl.

12. The method of claim 7, wherein Z is —C(O)OR³; and R³ is H.

13. The method of claim 7, wherein Z is —C(O)OR³; and R³ is C₁₋₆ alkyl.

14. The method of claim 1, wherein the compound is
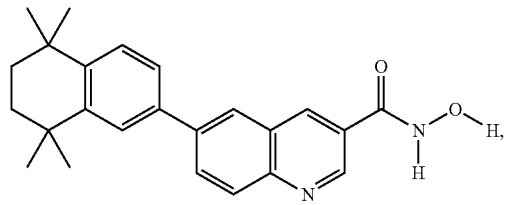
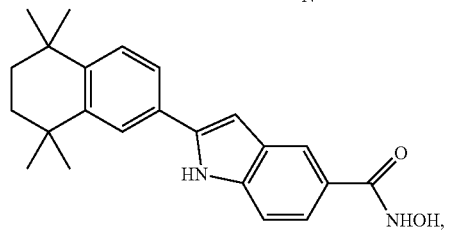
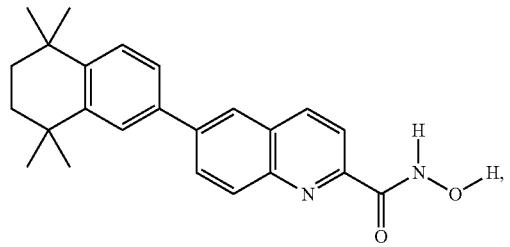
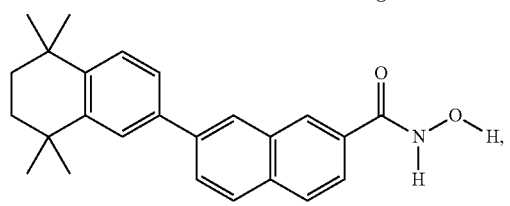
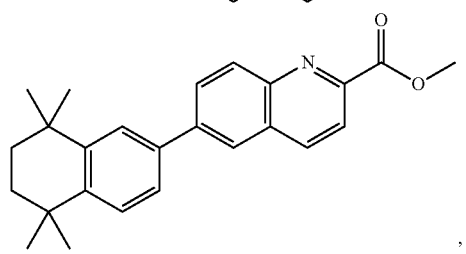
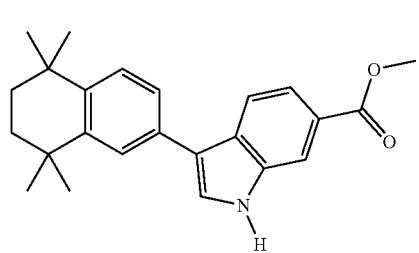
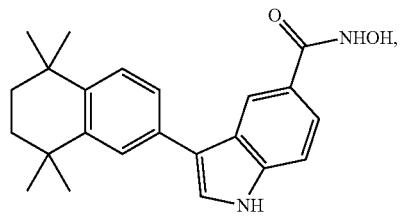
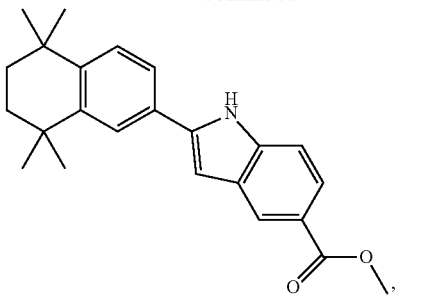
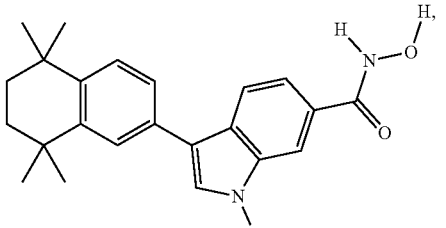
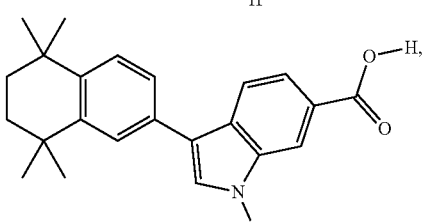
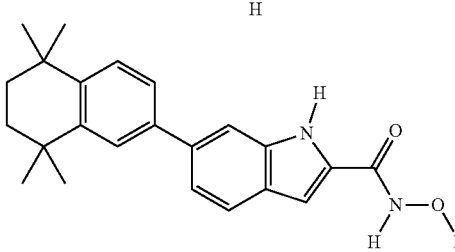
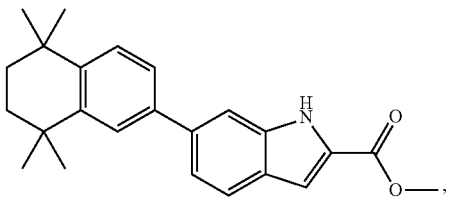
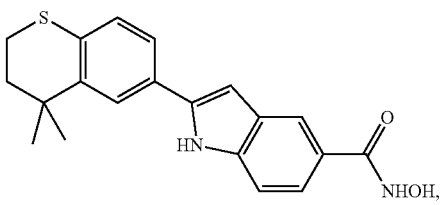
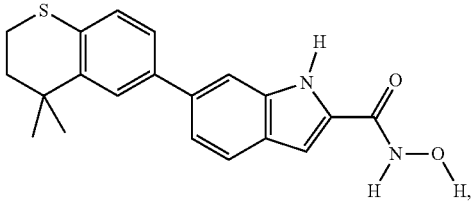

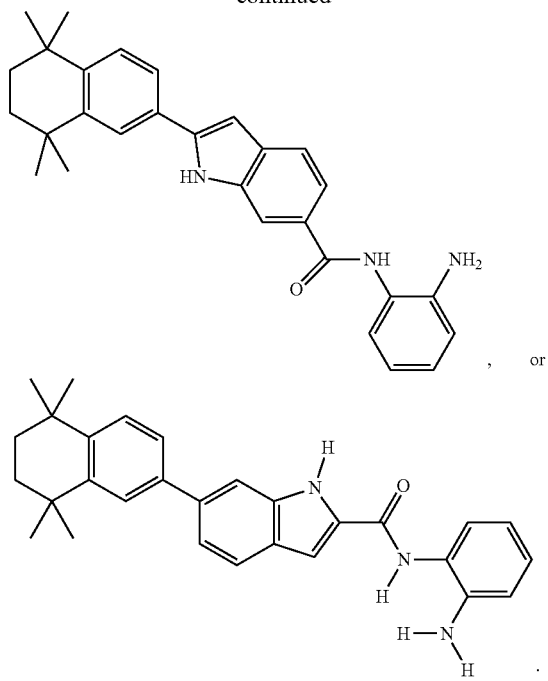

15. The method of claim 1, wherein the cancer is non-small cell lung cancer, colon cancer, melanoma, breast cancer, renal cancer, ovarian cancer, prostate cancer, cancer of the central nervous system, a blood cancer, or a neuroblastoma.

16. The method of claim 1, wherein the non-malignant tumor is pheochromocytoma.

17. The method of claim 1, wherein the cancer is a breast cancer or a neuroblastoma.

18. The method of claim 17, wherein:
W is a indolinylene linked to A at any one of positions 2, 3, 4, 5, 6, or 7 of the indolinylene; Z is —C(O)NR$^1$R$^2$ or —C(O)OR$^3$, wherein R$^1$ and R$^2$ are each independently hydrogen, hydroxyl, $C_{1-6}$ alkyl, hydroxy$C_{1-6}$ alkyl, amino$C_{1-6}$ alkyl, or aminoaryl; and R$^3$ is H or $C_{1-6}$ alkyl, and wherein Z is linked to the indolinylene at any one of positions 2, 3, 4, 5, 6, or 7 of the indolinylene not linked to A.

19. The method of claim 17, wherein:
W is a quinolinene linked to A at any one of positions 2, 3, 4, 5, 6, 7 or 8 of the quinolinene ; Z is —C(O)NR$^1$R$^2$ or —C(O)OR$^3$, wherein R$^1$ and R$^2$ are each independently hydrogen, hydroxyl, $C_{1-6}$ alkyl, hydroxy$C_{1-6}$ alkyl, amino$C_{1-6}$ alkyl, or aminoaryl; and R$^3$ is H or $C_{1-6}$ alkyl, and wherein Z is linked to the quinolinene at any one of positions 2, 3, 4, 5, 6, 7 or 8 of the quinolinene.

* * * * *